US007592177B2

(12) United States Patent
Chen et al.

(10) Patent No.: US 7,592,177 B2

(45) Date of Patent: Sep. 22, 2009

(54) COMPOSITIONS AND METHODS FOR INDUCING CELL DEDIFFERENTIATION

(75) Inventors: Shuibing Chen, San Diego, CA (US); Sheng Ding, San Diego, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 280 days.

(21) Appl. No.: 10/985,645

(22) Filed: Nov. 10, 2004

(65) Prior Publication Data

US 2005/0176707 A1 Aug. 11, 2005

Related U.S. Application Data

(60) Provisional application No. 60/518,947, filed on Nov. 10, 2003.

(51) Int. Cl.

*C07D 473/32* (2006.01)
*A61K 31/52* (2006.01)
*C12N 5/08* (2006.01)

(52) U.S. Cl. ....................... 435/377; 544/118; 544/277; 424/9.2; 514/234.2

(58) Field of Classification Search .............. 514/234.2, 514/263.22, 263.37, 263.4; 544/234.2, 276, 544/277, 118; 435/377

See application file for complete search history.

(56) References Cited

U.S. PATENT DOCUMENTS

| | | | | |
|---|---|---|---|---|
| 5,153,318 A * | 10/1992 | Rideout et al. | ........... | 536/27.61 |
| 5,942,225 A | 8/1999 | Bruder et al. | | |
| 6,255,485 B1 | 7/2001 | Gray et al. | | |
| 6,369,029 B1 | 4/2002 | Andress et al. | | |
| 6,589,950 B1 | 7/2003 | Collingwood et al. | | |
| 7,041,824 B2 * | 5/2006 | Bordon-Pallier et al. | .... | 544/277 |
| 2002/0016329 A1 | 2/2002 | Imbach et al. | | |
| 2003/0225278 A1 | 12/2003 | Ciszewski et al. | | |
| 2007/0254884 A1 * | 11/2007 | Chen et al. | .................. | 514/247 |

FOREIGN PATENT DOCUMENTS

| | | | |
|---|---|---|---|
| FR | 2 793 794 A1 | 11/2000 | |
| WO | WO 00/71543 A1 | 11/2000 | |
| WO | WO 02/051843 A1 | 7/2002 | |

OTHER PUBLICATIONS

Elion, Journal of Biological Chemistry (1951), 192, 505-18.*

Fiorini, Maria T.; Abell, Chris Tetrahedron Letters (1998), 39(13), 1827-1830.*

Basyouni, W.M., et al., "Synthesis and Antimicrobial Activity of Some New 6-Substituted 9-Arylpurine Derivatives," *Egyptian J. Chem.*, 1999, vol. 42, No. 6, pp. 587-598.

Chen, S., et al., "Dedifferentiation of Lineage-Committed Cells by a Small Molecule," *J. Am. Chem. Soc.*, 2004, vol. 126, pp. 410-411.

Imbach, P., et al., "2,6,9-Trisubstituted Purines: Optimization Towards Highly Potent and Selective CDK1 Inhibitors," *Bioorganic & Medicinal Chemistry Letters*, 1999, vol. 9, pp. 91-96.

Kelley, J., et al., "Antirhinovirus Activity of 6-Anilino-9-benzyl-2-chloro-9H-purines," *J. Med. Chem.* 1990, vol. 33, pp. 1360-1363.

Montgomery, J., et al., "Synthesis of Potential Anticancer Agents. XXVI. The Alkylation of 6-Chloropurine," Feb. 5, 1961, vol. 83, pp. 630-635.

Chen, Shuibing, et al., "Dedifferentiation of Lineage-Committed Cells by a Small Molecule," J. Am. Chem. Soc., 2004, vol. 126, pp. 410-411.

Gey, Claudia, et al., "Small Molecules, Big Plans—Can Low-Molecular-Weight Compounds Control Human Regeneration?" Angew. Chem. Int. Ed., 2004, vol. 43, No. 31, pp. 3998-4000.

Hildebrand, Catherine, et al., "Structure-Activity Relationships of $N^2$-Substituted Guanines as Inhibitors of HSV1 and HSV2 Thymidine Kinases," J. Med. Chem., 1990, vol. 33, pp. 203-206.

Medveczky, Maria, et al., "Haloanilino Derivatives of Pyrimidines, Purines, and Purine Nucleoside Analogs: Synthesis and Activity against Human Cytomegalovirus," J. Med. Chem. 1995, vol. 38, pp. 1811-1819.

Wright, George E., et al., "Synthesis, Cell Growth Inhibition, and Antitumor Screening of 2-(*p*-*n*-Butylanilino) purines and Their Nucleoside Analogues," J. Med. Chem. 1987, vol. 30, pp. 109-116.

* cited by examiner

*Primary Examiner*—Mark L Berch

(74) *Attorney, Agent, or Firm*—Townsend and Townsend and Crew LLP

(57) ABSTRACT

The present invention provides compositions and methods for dedifferentiating lineage committed mammalian cells.

20 Claims, 2 Drawing Sheets

(Compound A)

COMPOSITIONS AND METHODS FOR INDUCING CELL DEDIFFERENTIATION

CROSS-REFERENCES TO RELATED APPLICATIONS

This application claims benefit of U.S. Provisional Application No. 60/518,947, filed Nov. 10, 2003, which application is incorporated herein by reference for all purposes.

BACKGROUND OF THE INVENTION

In mammals, regeneration of injured tissues and limbs is largely limited by an irreversible differentiation process (see, e.g., Carlson, *Dev. Dyn.* 226(2):167-81 (2003)). As a consequence, stem cells, in particular embryonic stem cells (ESCs) which can be expanded indefinitely and are pluripotent or multipotent, have attracted considerable attention as a therapeutic approach to the damage caused by cardiovascular disease, neurodegenerative disease and aging (see, e.g., Committee on the Biological and Biomedical Applications of Stem Cell Research, *Stem Cells and the Future of Regenerative Medicine* 2002, the National Academies Press, Washington, D.C.). However the use of stem cells in cell replacement therapy remains problematic for a number of reasons, including the lack of a reliable source for stem cells. For example, multipotent human mesenchymal stem cells (MSC) may be isolated from the bone marrow; a large amount of donor bone marrow is required to obtain sufficient quantities of stem cells for most therapeutic or research applications.

The ability to dedifferentiate or reverse lineage-committed cells to multipotent progenitor cells (i.e. multipotent stem cells) overcome many of these obstacles. With an efficient dedifferentiation process, it is conceivable that healthy, abundant and easily accessible adult cells could be used to generate different types of functional cells for repair of damaged tissues. Moreover, recent studies of the plasticity of murine myotubes and other cells derived from adult tissues suggest that dedifferentiation may be possible in mammalian system (see, e.g., Odelberg et al., *Cell* 103:1099-1109 (2000); McGann et al., *Proc. Natl. Acad. Sci. USA* 98:13699-13704 (2001); and Tsai et al. *Developmental Cell* 2:707-712 (2002)). However, in contrast to the differentiation process, compositions and methods for the control and study of dedifferentiation are lacking.

Cell-based phenotypic assays and, more recently, pathway screens of synthetic small molecules and natural products have historically provided very useful chemical probes of complex cellular processes (see, e.g., White, D. J. G. Ed., *Proceedings of an International Conference on Cyclosporin A* (Elsevier, Amsterdam, 1982), 5-19). The identification of small molecules which induce dedifferentiation of mammalian somatic cells should help to elucidate the molecular mechanism of this phenomenon, and may ultimately allow in vivo tissue regeneration.

Thus, there is a need in the art for compositions and methods for inducing dedifferentiation of lineage committed mammalian cells into multipotent or pluripotent stem cells. The present invention satisfies these and other needs.

BRIEF SUMMARY OF THE INVENTION

The present invention provides novel compositions and methods for inducing dedifferentiation of lineage committed mammalian cells into multipotent stem cells.

One embodiment of the present invention provides a compound of Formula I:

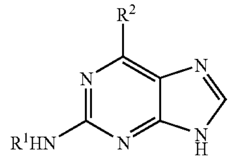

I

In Formula I, $R^1$ is a member selected from the group consisting of hydrogen, $C_{1-4}$alkyl, $C_{3-8}$cycloalkyl and $C_{0-2}$alkylaryl, substituted with 0-2 $R^{1a}$ groups that are independently selected from the group consisting of halogen, $C_{1-4}$alkyl, $C_{1-4}$alkoxy, —N($R^{1b}$, $R^{1b}$), —$SO_2$N($R^{1b}$, $R^{1b}$), —C(O)N($R^{1b}$, $R^{1b}$) and —O-aryl, or when said $R^{1a}$ groups are on adjacent ring atoms they are optionally taken together to form a member selected from the group consisting of —O—$(CH_2)_{1-2}$—O—, —O—$C(CH_3)_2CH_2$— and —$(CH_2)_{3-4}$—, or $R^1$ is optionally together with the nitrogen to which it is attached to form a heterocycle, optionally substituted with $C_{1-4}$alkyl, $C_{3-8}$cycloalkyl, $C_{1-4}$alkylhydroxy and $C_{0-2}$alkylaryl; and each $R^{1b}$ group is independently selected and is a functional group including, but not limited to, hydrogen and $C_{1-4}$alkyl.

In Formula I, $R^2$ is a functional group including, but not limited to, hydrogen, halogen and -L-$R^3$; L is a functional group including, but not limited to, —O—, —S—, —$S(O)_2$— and —$NR^4$—, wherein $R^4$ is H, or $R^4$ is optionally taken together with $R^3$ and the nitrogen to which both are attached to form a heterocycle, optionally substituted with $C_{1-4}$alkyl; $R^3$ is a functional group including, but not limited to, $C_4$ alkyl, cyclohexyl, piperidinyl and aryl-$C_{0-2}$ alkyl, cyclohexen-2,3-yl-ethyl, and cyclohexylmethyl, substituted with 0-2 $R^{3a}$ groups that are independently selected and are functional groups including, but not limited to, halogen, $C_{1-4}$alkyl, $C_{1-4}$alkoxy, —N($R^{3b}R^{3b}$), —$SO_2$N($R^{3b}R^{3b}$), —C(O)N($R^{3b}R^{3b}$), arylalkyl-, 2,3-dihydro-benzofuranyl-meth-2-yl, 2,2-diphenyleth-1-yl,-, —C(O)OEt and —O-aryl, or when the $R^{3a}$ groups are on adjacent ring atoms they are optionally taken together to form a member selected from the group consisting of —O—$(CH_2)_{1-2}$—O—, —O—$C(CH_3)_2$ $CH_2$— and —$(CH_2)_{3-4}$—; and each $R^{3b}$ group is a member that is independently selected and is a functional group including, but not limited to, hydrogen and $C_{1-4}$alkyl.

The compounds of the present invention include all pharmaceutically acceptable salts, isomers, solvates, hydrates and prodrugs thereof.

A further embodiment of the present invention provides a method for inducing dedifferentiation of a lineage committed cell. A lineage committed mammalian cell is contacted with a compound of Formula I, whereby the mammalian cell dedifferentiates into a multipotent stem cell. In some embodiments, the method further comprises detecting dedifferentiation of the mammalian cell into a multipotent stem cell (e.g., by detecting loss of expression of a marker gene expressed by the lineage committed mammalian cell). In some embodiments, the lineage committed mammalian cell is a myoblast cell.

Even a further embodiment of the present invention provides a method for identifying compounds that induce dedifferentiation of lineage committed mammalian cells into multipotent stem cells. A lineage committed mammalian cell is contacted with a test compound suspected of inducing dedifferentiation of lineage committed cells. The cells are cultured in a first cell culture media that induces differentiation of the multipotent stem cell into a first cell type and a second cell culture media that induces differentiation of the multipotent stem cell into a second cell type. It is determined whether the cells have undergone differentiation into the first or second cell type, wherein induction of differentiation into both the first cell type and the second cell type identifies the test compound as a compound that induces dedifferentiation of lineage committed mammalian cells. In some embodiments of the invention, the first cell culture medium induces osteogenesis and the second culture medium induces adipogenesis, and the first cell type is an osteoblast and the second cell type is an adipocyte. In some embodiments, the test compound is a member selected from the group consisting of: substituted purines (e.g., a 2,6 disubstituted purine), pyrimidines, quinazolines, pyrazines, pyrrolopyrimidine, pyrazolopyrimidine, phthalazines, pyridazines, and quinoxalines. In some embodiments, induction of osteogenesis is detected by detecting expression of an osteogenesis marker gene (e.g., alkaline phosphatase, collagen type I, osteocalcin, ad osteoponin) and induction of adipogenesis is detected by detecting expression of an adipogenesis marker gene (e.g., ob, Ucp, PPARγ and C/EBPs (see, e.g., Kozak and Kozak, *Endocrinology* 134(2):906-13 (1994) and Lee et al., *J. Clin. Invest.* 111 (4): 453-461 (2003).

In yet another embodiment, the present invention provides a method of treating a bone disorder (e.g., osteoporosis, rickets, osteomalacia, McCune-Albright syndrome, or Paget's disease). A mammalian cell is contacted with a compound of Formula I, whereby the mammalian cell dedifferentiates into a multipotent stem cell. The multipotent stem cell is cultured in a cell culture medium that induces differentiation of the multipotent stem cell into a cell of an osteoblast lineage. In some embodiments, the cell culture medium that induces differentiation of the multipotent stem cell into a cell of an osteoblast lineage comprises ascorbic acid, dexamethasone, and β-glycerophosphate. In some embodiments, the mammalian cell is attached to a solid support (e.g., a three dimensional matrix or a planar surface). In some embodiments, administration is by surgical implantation.

Other embodiments and advantages of the present invention will be apparent from the detailed description that follows.

DETAILED DESCRIPTION OF THE INVENTION

I. Introduction

Figure 1:
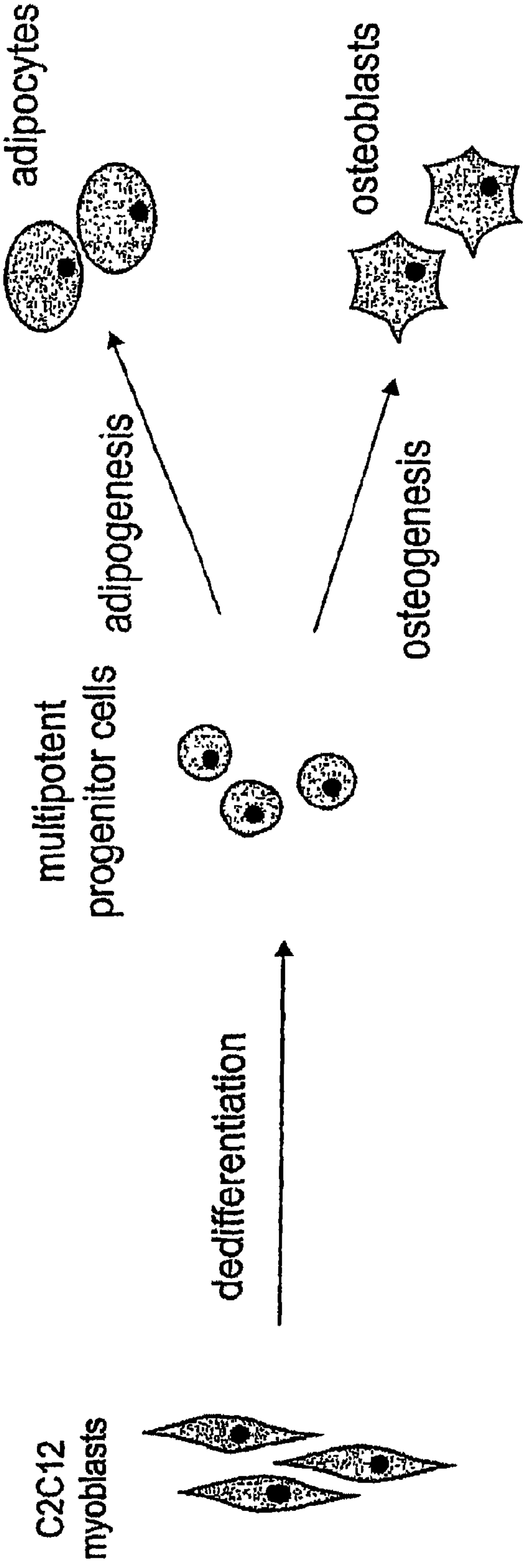
FIG. 1 illustrates the screening method used to identify compounds with dedifferentiation inducing activity.

The present invention provides compounds, compositions and methods for dedifferentiating lineage committed mammalian cells into stem cells (e.g., multipotent or pluripotent cells). More particularly, the present invention provides compounds of Formula I that are useful for dedifferentiating a lineage committed mammalian cells into stem cells. In some embodiments, a composition comprising the compound of Formula I is provided. In other embodiments, methods of inducing dedifferentiation of lineage committed mammalian cells into stem cells are provided. In other embodiment, the stem cells are further differentiated into a linage committed cell. In even further embodiments, methods of identifying additional compounds useful for inducing dedifferentiaton of lineage committed cells into stem cells are provided.

II. Definitions

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by $-CH_2CH_2CH_2CH_2-$, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include $-CH_2-CH_2-O-CH_3$, $-CH_2-CH_2-O-CH_2-CH_2-(CH_3)_2$, $-CH_2-CH_2-NH-CH_3$, $-CH_2-CH_2-N(CH_3)-CH_3$, $-CH_2-S-CH_2-CH_3$, $-CH_2-CH_2,-S(O)-CH_3$, $-CH_2-CH_2-S(O)_2-CH_3$, $-CH{=}CH-O-CH_3$, $-Si(CH_3)_3$, $-CH_2-CH{=}N-OCH_3$, and $-CH{=}CH-N(CH_3)-CH_3$. Up to two heteroatoms may be consecutive, such as, for example, $-CH_2-NH-OCH_3$ and $-CH_2-O-Si(CH_3)_3$. Similarly, the term "heteroalkylene" by itself or as part of another substituent means a divalent radical derived from heteroalkyl, as exemplified by $-CH_2-CH_2-S-CH_2CH_2-$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R"', —OC(O)R', —C(O)R', $—CO_2R'$, —CONR'R", —OC(O)NR'R", —NR"C(O)R', —NR'—C(O)NR"R"', $—NR"C(O)_2R'$, $—NH—C(NH_2)=NH$, $—NR'C(NH_2)=NH$, $—NH—C(NH_2)=NR'$, —S(O)R', $—S(O)_2R'$, $—S(O)_2NR'R"$, —CN and $—NO_2$ in a number ranging from zero to (2m'+1), where m' is the total number of carbon atoms in such radical. R', R" and R"' each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. As used herein, R', and R" are fully applicable to $R^{3a}$ and $R^{3b}$. From the above discussion of substituents, one of skill in the art will understand that the term "alkyl" is meant to include groups such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similarly, substituents for the aryl and heteroaryl groups are varied and are selected from: -halogen, —OR', —OC(O)R', —NR'R", —SR', —R', —CN, $—NO_2$, $—CO_2R'$, —CONR'R", —C(O)R', —OC(O)NR'R", —NR"C(O)R', $—NR"C(O)_2R'$, —NR'—C(O)NR"R"', $—NH—C(NH_2)=NH$, $—NR'C(NH_2)=NH$, $—NH—C(NH_2)=NR'$, —S(O)R', $—S(O)_2R'$, $—S(O)_2NR'R"$, $—N_3$, $—CH(Ph)_2$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula $-T-C(O)—(CH_2)_q—U—$, wherein T and U are independently —NH—, —O—, $—CH_2—$ or a single bond, and q is an integer of from 0 to 2. Alternatively, two of the substituents on adjacent atoms of the aryl or heteroaryl ring may optionally be replaced with a substituent of the formula $-A-(CH_2)_r—B—$, wherein A and B are independently $—CH_2—$, —O—, —NH—, —S—, —S(O)—, $—S(O)_2—$, $—S(O)_2NR'—$ or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula $—(CH_2)_s—X—(CH_2)_t—$, where s and t are independently integers of from 0 to 3, and X is —O—, —NR'—, —S—, —S(O)—, $—S(O)_2—$, or $—S(O)_2NR'—$. The substituent R' in —NR'— and $—S(O)_2NR'—$ is selected from hydrogen or unsubstituted ($C_1$-$C_6$)alkyl.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

As used herein, the term "heteroatom" is meant to include oxygen (O), nitrogen (N) and sulfur (S).

As used herein, the abbreviations "Me" and "Ph", are used to represent a methyl group and phenyl group, respectively.

The term “pharmaceutically acceptable salts” is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, “Pharmaceutical Salts”, *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 (125I) or carbon-14 ($^{14}C$). All isotopic variations of the compounds of the present invention, whether radioactive or not, are intended to be encompassed within the scope of the present invention.

A “lineage committed cell” as used herein, refers to any cell that has or will differentiate into a particular cell type or related cell types. Lineage committed cells include, for example, osteoblasts, myoblasts, chrondrocytes, and adipocytes.

A “stem cell,” as used herein, refers to any self-renewing pluripotent cell or multipotent cell or progenitor cell or precursor cell that is capable of differentiating into multiple cell types. Stem cells include those that are capable of differentiating into cells of osteoblast lineage, a mesenchymal cell lineage (e.g., bone, cartilage, adipose, muscle, stroma, including hematopoietic supportive stroma, and tendon).

“Differentiate” or “differentiation,” as used herein, refers to the process by which precursor or progenitor cells (i.e., stem cells) differentiate into specific cell types, e.g., osteoblasts. Differentiated cells can be identified by their patterns of gene expression and cell surface protein expression. For example, cells of an osteoblast lineage typically express the following genes: alkaline phosphatase, collagen type I, osteocalcin, and osteoponin, and the following bone specific transcription factors: Cbfa1/Runx2, Osx, gsc, Dlx1, Dlx5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, 2000 supra and Nakashima et al., *Cell* 108(1):17-29 (2002). As a further example, cells of a myoblast lineage typically express the following genes: MyoD, Myf5, myosin, CD56, and desmin (see, e.g., Stewart et al., *J. Cell Physiol.* 196(1):70-8 (2003)). As another example, cells of an adipocyte lineage typically express the following genes: ob, Ucp, PPARγ and C/EBPs (see, e.g., Kozak and Kozak, *Endocrinology* 134(2):906-13 (1994)) and Lee et al., *J. Clin. Invest.* 111 (4): 453-461 (2003).

“Dedifferentiate” or “dedifferentiation,” as used herein, refers to the process by which lineage committed cells (e.g., myoblasts or osteoblasts) reverse their lineage commitment and become precursor or progenitor cells (i.e., multipotent or pluripotent stem cells). Dedifferentiated cells can be identified by loss of patterns of gene expression and cell surface protein expression associated with the lineage committed cells. For example, myoblasts typically express, inter alia, MyoD, Myf5, myosin, CD56 and desmin. A loss of expression or decrease in expression levels of one or more of these genes indicates that a myoblast has undergone dedifferentiation.

“Transdifferentiation” refers to the process refers to the process by which precursor or progenitor cells (i.e., stem cells) pre-committed to cell types of one lineage differentiate into specific cell types of another lineage, e.g., pre-adipocytes transdifferentiate into osteoblasts or myoblasts transdifferentiate into osteoblasts. Transdifferentiated cells can be identified by their patterns of gene expression and cell surface protein expression. Typically, cells of an osteoblast lineage express genes such as, for example, alkaline phosphatase, collagen type I, osteocalcin, and osteoponin; and bone specific transcription factors such as, for example, Cbfa1/Runx2, Osx, gsc, Dlx1, Dlx5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, 2000 supra and Nakashima et al., *Cell* 108(1):17-29 (2002).

“Osteogenesis,” as used herein, refers to proliferation of bone cells and growth of bone tissue (i.e., synthesis and deposit of new bone matrix). Osteogenesis also refers to differentiation or transdifferentiation of progenitor or precursor cells into bone cells (i.e., osteoblasts). Progenitor or precursor cells can be pluripotent stem cells such as, e.g., mesenchymal stem cells. Progenitor or precursor cells can be cells pre-committed to an osteoblast lineage (e.g., pre-osteoblast cells) or cells that are not pre-committed to an osteoblast lineage (e.g., pre-adipocytes or myoblasts).

A "solid support," as used herein in connection with inducing osteogenesis, refers to a three-dimensional matrix or a planar surface on which the stem cells can be cultured. The solid support can be derived from naturally occurring substances (i.e., protein based) or synthetic substances. For example, matrices based on naturally occurring substances may be composed of autologous bone fragments or commercially available bone substitutes as described in e.g., Clokie et al., *J. Craniofac. Surg.* 13(1):111-21 (2002) and Isaksson, *Swed. Dent. J. Suppl.* 84:1-46 (1992). Suitable synthetic matrices are described in, e.g., U.S. Pat. Nos. 5,041,138, 5,512,474, and 6,425,222. For example, biodegradable artificial polymers, such as polyglycolic acid, polyorthoester, or polyanhydride can be used for the solid support. Calcium carbonate, aragonite, and porous ceramics (e.g., dense hydroxyapatite ceramic) are also suitable for use in the solid support. Polymers such as polypropylene, polyethylene glycol, and polystyrene can also be used in the solid support. Cells cultured and differentiated on a solid support that is a three-dimensional matrix typically grow on all of the surfaces of the matrix, e.g., internal and external. Cells cultured and differentiated on a solid support that is planar typically grow in a monolayer. The term "solid-support" is also used in the context of preparing the compounds of Formula I. In this context, "solid-support" refers to a polymeric support, such as a bead, that can be partially soluble in a suitable solvent or completely insoluble, and is used to bind, for example, a reactant or a reagent of the reaction. Suitable solid-supports include, but are not limited to, PAL resin, Wang resin, and polystyrene resin.

"Culturing," as used herein, refers to maintaining cells under conditions in which they can proliferate, differentiate, and avoid senescence. Cells can be cultured in growth media containing appropriate growth factors.

III. Compounds of the Present Invention and Methods for their Preparation

A. The Compounds of Formula I

In one aspect, the present invention provides compounds of Formula I:

I

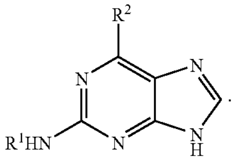

In Formula I, $R^1$ is a functional group including, but not limited to, hydrogen, $C_{1-4}$alkyl, $C_{3-8}$cycloalkyl and $C_{0-2}$alkylaryl, substituted with 0-2 $R^{1a}$ groups that are each independently selected and are functional groups including, but not limited to, halogen, $C_{1-4}$alkyl, $C_{1-4}$alkoxy, —N($R^{1b}$, $R^{1b}$), —$SO_2N$($R^{1b}$, $R^{1b}$), —C(O)N($R^{1b}$, $R^{1b}$) and —O-aryl, or when the $R^{1a}$ groups are on adjacent ring atoms they are optionally taken together to form a member selected from the group consisting of —O—$(CH_2)_{1-2}$—O—, —O—$C(CH_3)_2CH_2$— and —$(CH_2)_{3-4}$—, or $R^1$ is optionally taken together with the nitrogen to which it is attached to form a heterocycle, optionally substituted with a functional group including, but not limited to, $C_{1-4}$alkyl, $C_{3-8}$cycloalkyl, $C_{1-4}$alkylhydroxy and $C_{0-2}$alkylaryl; and each $R^{1b}$ group is independently selected and is a functional group including, but not limited to, hydrogen and $C_{1-4}$alkyl.

In Formula I, $R^2$ is a functional group including, but not limited to, hydrogen, halogen and -L-$R^3$; L is a functional group including, but not limited to, —O—, —S—, —$S(O)_2$— and —$NR^4$—, wherein $R^4$ is H, or $R^4$ is optionally taken together with $R^3$ and the nitrogen to which both are attached to form a heterocycle, optionally substituted with $C_{1-4}$alkyl; $R^3$ is a functional group including, but not limited to, $C_4$ alkyl, cyclohexyl, piperidinyl and aryl-$C_{0-2}$ alkyl, cyclohexen-2,3-ethyl, and cyclohexylmethyl, substituted with 0-2 $R^{3a}$ groups that are independently selected and that are functional groups including, but not limited to, halogen, $C_{1-4}$alkyl, $C_{1-4}$alkoxy, —N($R^{3b}R^{3b}$), —$SO_2N$($R^{3b}R^{3b}$), —C(O)N($R^{3b}R^{3b}$), arylalkyl-, 2,3-dihydro-benzofuranyl-meth-2-yl, 2,2-diphenyleth-1-yl,-, —C(O)OEt and —O-aryl, or when the $R^{3a}$ groups are on adjacent ring atoms, they are optionally taken together to form a member selected from the group consisting of —O—$(CH_2)_{1-2}$—O—, —O—$C(CH_3)_2CH_2$— and —$(CH_2)_{3-4}$—; and each $R^{3b}$ group is independently selected and is a functional group including, but not limited to, hydrogen and $C_{1-4}$alkyl.

The compounds of the present invention include all pharmaceutically acceptable salts, isomers, solvates, hydrates and prodrugs thereof.

In a preferred embodiment, $R^1$ is a functional group including, but not limited to, the following:

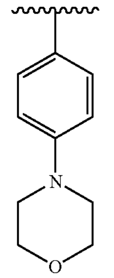,
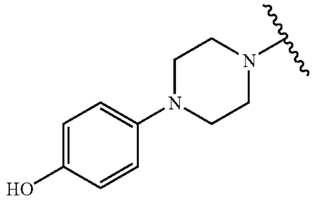,
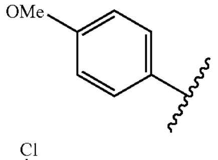,
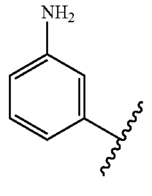,
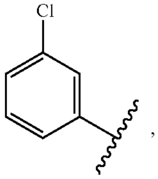,
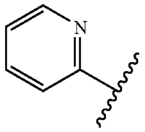, and
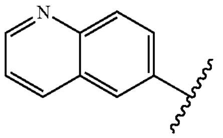
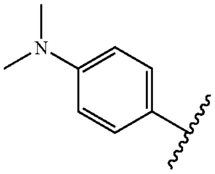.

In a preferred embodiment, $R^2$ is a functional group including, but not limited to, the following:

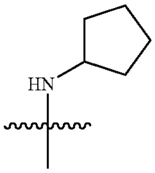
,
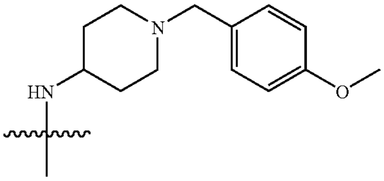
,
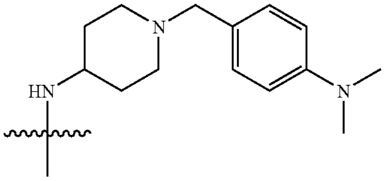
,
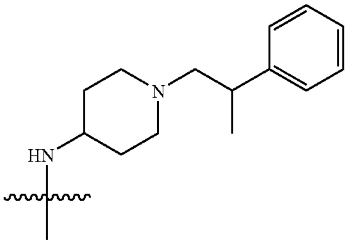
,
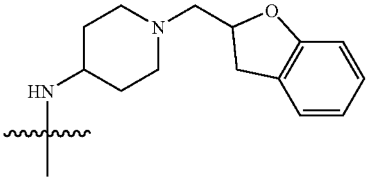
,
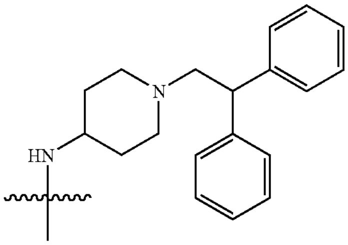
,
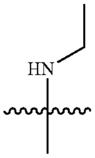
,
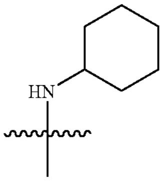
,
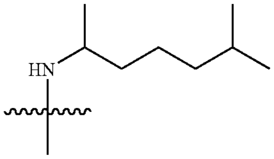
,
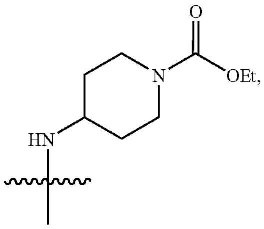
,
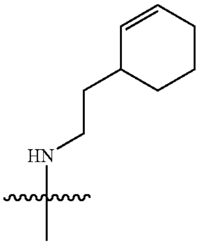
, -continued

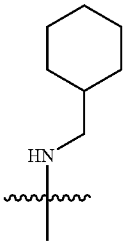
,
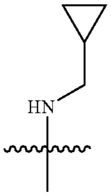
,
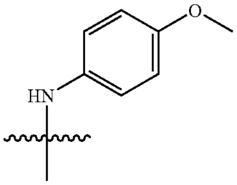
,
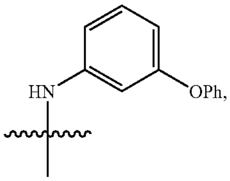
,
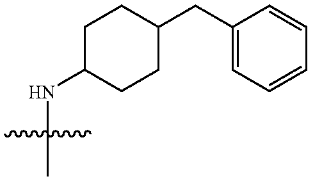
,
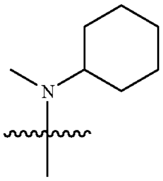
, and
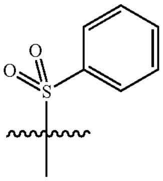
.

In some preferred embodiments, $R^1$ is $C_{0-2}$alkylaryl. In other preferred embodiments, $R^1$ is $C_{0-2}$alkylaryl, substituted with —N($R^{1b}$, $R^{1b}$).

In some embodiments, $R^1$ is

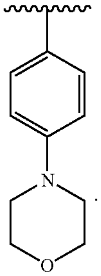
.

In some embodiments, $R^2$ is -L-$R^3$. In some embodiments, L is —$NR^4$—, wherein $R^4$ is hydrogen, and $R^3$ is $C_{3-8}$cycloalkyl. In some embodiments, $R^3$ is cyclohexyl.

Preferred compounds of the present invention, include, but are not limited to the following compounds:
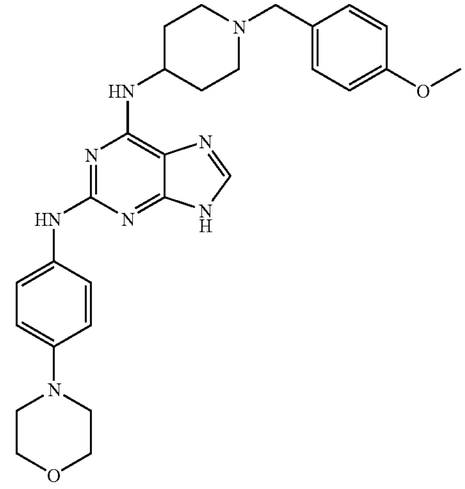
,
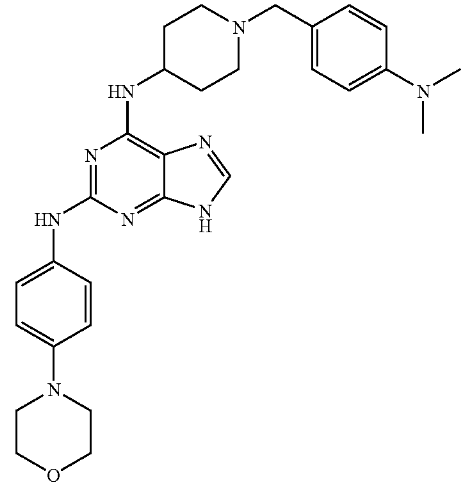
,
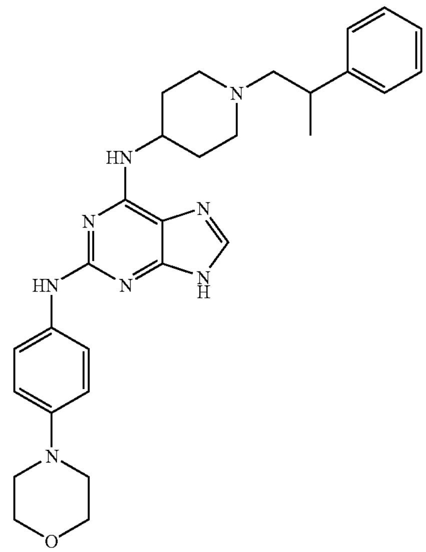
,
-continued
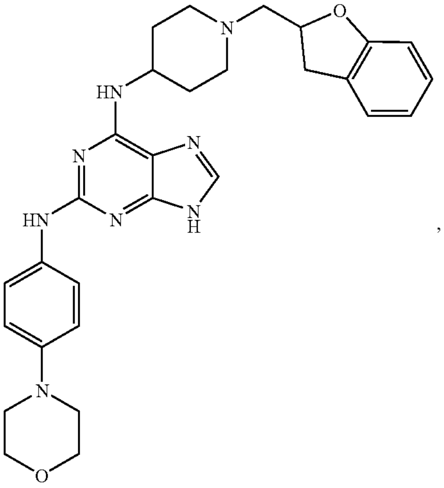
,
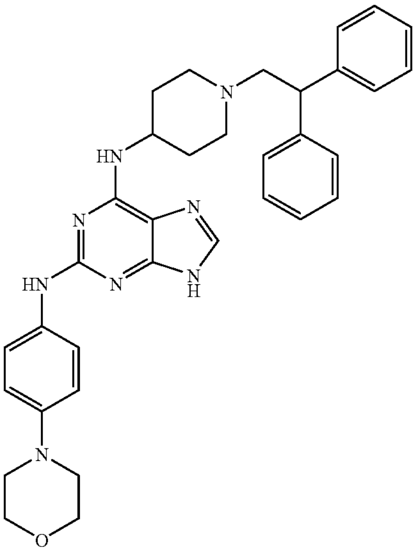
,
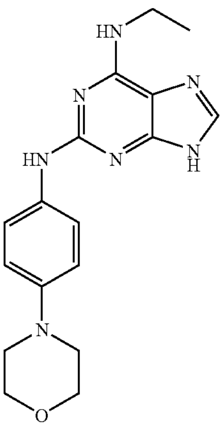
,
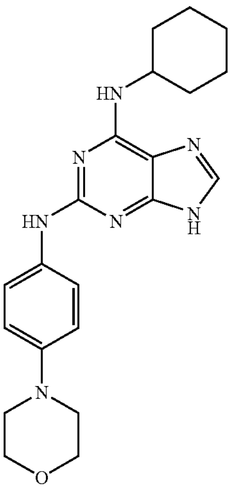
, -continued
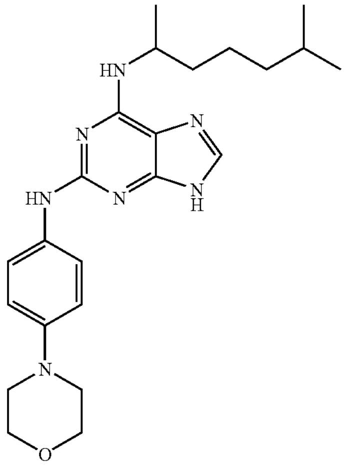
,
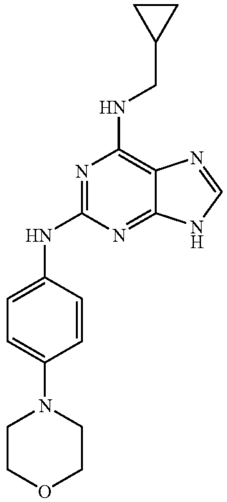
,
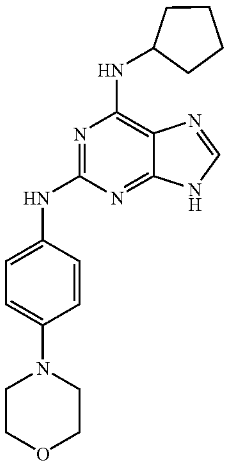
,
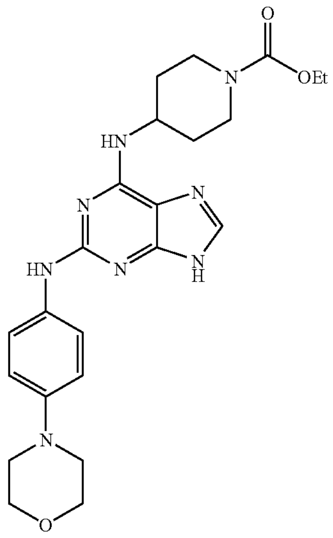
,
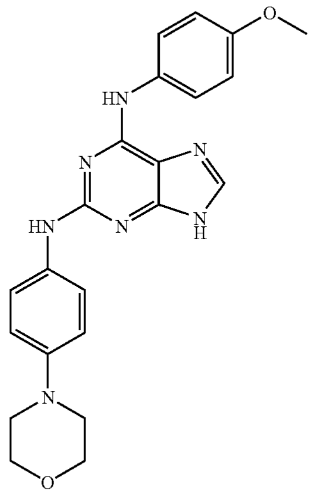
and
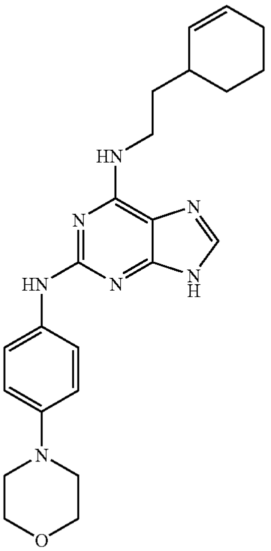
,
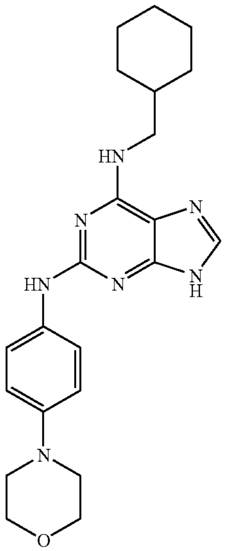
,
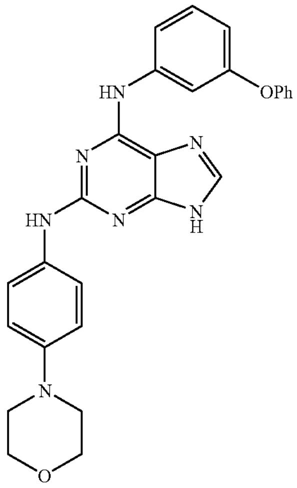
.

In a particularly preferred embodiment, the compound has the following structure:

(Compound A)

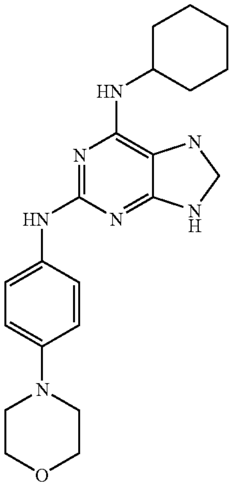

.

The compounds of Formula I can be readily screened for their ability to induce dedifferentiation of lineage committed mammalian cells (i.e., to generate stem cells) using the screening methods set forth below and, in particular, in the examples.

B. Preparation of Compounds

The compounds of the present invention can be prepared by either solid-phase or solution-phase synthesis.

1. Solid-Phase Synthesis

Methods directed to the solid-phase synthesis of the compounds of Formula I are discussed herein in Example I, as well as in Ding et al., *J. Am. Chem. Soc.* 124:1594 (2002) and in U.S. patent application Ser. No. 10/687,220, filed on Oct. 15, 2003, U.S. Patent Application No. 60/328,763, filed Oct. 12, 2001, U.S. Patent Application No. 60/331,835, filed Nov. 20, 2001, U.S. Patent Application No. 60/346,480, filed Jan. 7, 2002, U.S. Patent Application No. 60/348,089, filed Jan. 10, 2002, and U.S. patent application Ser. No. 10/270,030, filed Oct. 12, 2002.

In one aspect, the present invention provides a method for synthesizing a substituted heteroaryl, the method comprising: (a) providing a dihaloheteroaryl scaffold moiety; and (b) capturing the dihaloheteroaryl scaffold moiety on a resin by nucleophilic substitution of a first halogen by a resin-bound amine nucleophile to afford a substituted heteroaryl, e.g., a resin-bound amine substituted monohaloheteroaryl; (c) reacting the second halogen with a suitably substituted amine or aryl alcohol to afford the resin bound substituted heteroaryl; and (d) cleavage of the substituted heteroaryl from the resin.

Suitable resins useful for the present invention include, but are not limited to, PAL resin, Wang resin, and polystyrene resin. Other suitable resins would be clear to a person of skill in the art. In a preferred embodiment, the PAL resin is utilized.

In a preferred embodiment, the two halogens, i.e., halo groups, of the dihaloheteroaryl scaffold moiety are independently selected and include, but are not limited to, chloro, fluoro, bromo and iodo. In a presently preferred embodiments, the two halogens are chloro groups.

In a preferred embodiment, the method further comprises substitution of the second halogen of the dihaloheteroaryl scaffold moiety by nucleophilic displacement or, alternatively, by a coupling reaction. In a presently preferred embodiment, a coupling reaction is employed to carry out the substitution of the second halogen of the dihaloheteroaryl scaffold moiety. In this connection, the coupling reaction is preferably a palladium-mediated coupling reaction.

It will be readily apparent to those of skill in the art that the two halogens, i.e., halo groups, of the dihaloheteroaryl scaffold moiety can be substituted with a number of different functional groups. Suitable functional groups include, but are not limited to, anilines, phenols, amines and boronic acids. In a preferred embodiment, the functional groups include, but are not limited to, aryl boronic acids, anilines and phenols.

In the compounds of the present invention, N9 is preferably unsubstituted. If, however, it is desirable to substitute N9, one can perform an initial substitution of N9 prior to substitution of the first halogen of the dihaloheteroaryl scaffold moiety. In a preferred embodiment, the initial substitution is carried out using a reaction including, but not limited to, alkylation reactions, acylation reactions and coupling reactions.

Numerous dihaloheteroaryl scaffold moieties can be used in the methods of the present invention. Examples of suitable dihaloheteroaryl scaffold moieties include, but not limited to, purines, pyrimidines, quinazolines, pyrazines, phthalazines, pyradazines and quinoxalines. In preferred embodiments of the present invention, the dihaloheteroaryl scaffold is a purine.

When a palladium-catalyzed coupling reaction is employed to substitute the halo groups of the dihaloheteroaryl or the halo group of the resin-bound amine substituted monohaloheteroaryl, the palladium-catalyzed coupling reaction typically involves reacting the dihaloheteroaryl or the resin-bound amine substituted monohaloheteroaryl with a coupling agent in the presence of a solvent, a palladium catalyst, a base and a carbene or phosphine ligand. Suitable coupling agents include, but are not limited to, boronic acids, amines and alcohols. In a presently preferred embodiment, suitable coupling agents include, but are not limited to, aryl boronic acids, anilines and phenols.

In the above methods, carbene or phosphine ligands can be used. Examples of ligands suitable for use in the methods of the present invention include, but are not limited to, the following carbene and phosphine ligands:

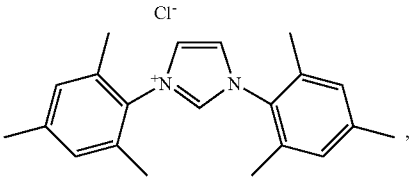

,

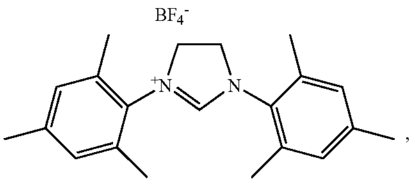

,

-continued

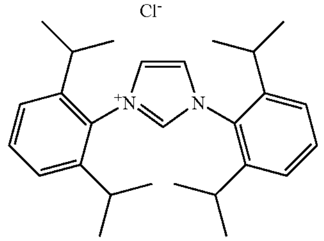

,

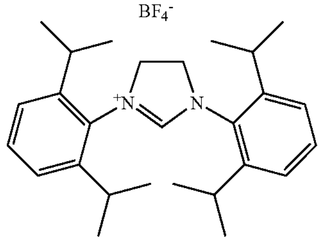

and

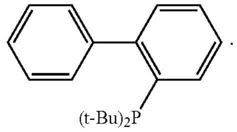

In a presently preferred embodiment, the ligand is a phosphine ligand including, but not limited to, the following:

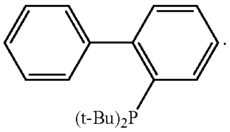

A number of bases can be used in carrying out the methods of the present invention. Examples of bases suitable for use in the above method include, but are not limited to, cesium carbonate, potassium carbonate, sodium carbonate, sodium bicarbonate, potassium bicarbonate, cesium bicarbonate, potassium fluoride, potassium phosphate, potassium tert-butyloxide, sodium tert-butyloxide, and triethylamine.

A number of solvents can be used in carrying out the methods of the present invention. Examples of solvents suitable for use in the above method include, but are not limited to, 1,4-dioxane, tetrahydrofuran, dimethoxyethane (DME), dimethylformamide (DMF), benzene and toluene.

A number of palladium catalysts can be used in carrying out the methods of the present invention. Typically, the oxidation state of the palladium in the catalyst is (0) or (II). Examples of palladium catalysts suitable for use in carrying out the methods of the present invention include, but are not limited to, $Pd_2(dba)_3$, $Pd(OAc)_2$, $Pd(PPh_3)_4$, Pd(O), $PdCl_2$ (dppf) and $PdCl_2$. Such catalysts are known to and used by those of skill in the art and, thus, their structures are known. In a preferred embodiment, the palladium catalyst is $Pd_2(dba)_3$.

In a preferred embodiment, the foregoing methods further comprise cleaving the compound from the solid support. It will be readily appreciated that the compounds of the present invention can be readily cleaved from the solid support using standard methods known to and used by those of skill in the art. Cleavage of a resin-bound compound and liberation of the desired compound from the resin is typically carried in the presence of an acid. Suitable acids include, but are not limited to, an organic acid such as formic acid, acetic acid, propionic acid, trichloroacetic acid, trifluoroacetic acid and the like, and inorganic acids such as hydrochloric acid, hydrobromic acid, sulfuric acid, hydrogen chloride, etc., or the like. The reaction is usually carried out in a solvent such as water, an alcohol such as methanol, ethanol, 1,4, dioxane, methylene chloride, tetrahydrofuran, a mixture thereof or any other solvent which does not adversely influence the reaction.

In yet another aspect of the present invention, the foregoing method is adapted to prepare a library (or an array) of heteroaryl scaffold moieties. Typically, the library of substituted scaffold moieties is prepared using a plurality of dihaloheteroaryl scaffold moieties. As such, in another aspect, the present invention provides a method for synthesizing a combinatorial library of substituted heteroaryls (e.g., heterocycles), the method comprising: providing a plurality of dihaloheterocyclic scaffold moieties; and capturing the dichloroheterocyclic scaffold moieties on a resin by nucleophilic substitution of a first chlorine by a resin-bound amine nucleophile).

In a preferred embodiment, the two halogens, i.e., halo groups, present in the dihaloheteroaryl scaffold moieties are independently selected and include, but are not limited to, chloro, fluoro, bromo and iodo. In a presently preferred embodiments, the two halogens of the dihaloheteroaryl scaffold moieties are chloro groups.

In a preferred embodiment, the method further comprises substitution of the second halogen of the dihaloheteroaryl scaffold moieties by nucleophilic displacement or, alternatively, by a coupling reaction. In a presently preferred embodiment, a coupling reaction is employed to carry out the substitution of the second halogen of the dihaloheteroaryl scaffold moieties. In this connection, the coupling reaction is preferably a palladium-mediated coupling reaction.

It will be readily apparent to those of skill in the art that the two halogens, i.e., halo groups, of the dihaloheteroaryl scaffold moieties can be substituted with a number of different functional groups, each of which is independently selected. Suitable functional groups include, but are not limited to, anilines, phenols, amines and boronic acids (see, Table I). In a presently preferred embodiment, the functional groups include, but are not limited to, aryl boronic acids, anilines and phenols.

If it is desirable to introduce a substitution at N9, the method further comprises performing initial substitutions prior to substitution of the first halogens of the dihaloheteroaryl scaffold moieties. In a preferred embodiment, the initial substitution is carried out using a reaction including, but not limited to, alkylation reactions, acylation reactions and coupling reactions.

Numerous dihaloheteroaryl scaffold moieties can be used in the methods of the present invention. Examples of suitable dihaloheteroaryl scaffold moieties include, but not limited to, purines, pyrimidines, quinazolines, pyrazines, phthalazines, pyradazines and quinoxalines.

When a palladium-catalyzed coupling reaction is employed to substitute the halo groups of the dihaloheteroaryl scaffold moieties or the halo group of the resin-bound amine substituted monohaloheteroaryls, the palladium-catalyzed coupling reaction typically involves reacting the dihaloheteroaryl or the resin-bound amine substituted monohaloheteroaryl with a coupling agent in the presence of a solvent, a palladium catalyst, a base and a carbene or phosphine ligand. Suitable coupling agents include, but are not limited to, boronic acids, amines and alcohols. In a presently preferred embodiment, suitable coupling agents include, but are not limited to, aryl boronic acids, anilines and phenols. It is noted that the foregoing discussions relating to the carbene or phosphine ligands, bases, solvents, palladium catalysts and copper catalysts set forth in connection with the methods for preparing a C-2 substituted purine compound are fully applicable to the methods for preparing a combinatorial library or array of substituted heteroaryl compound and, thus, they will not be repeated here.

2. Solution-Phase Synthesis

The solution-phase synthesis of the compounds of Formula I involves first substituting 2,6-dihaloheteroaryl with a suitably substituted amine under appropriate reaction conditions known to one of skill in the art. This is followed by substitution with a suitably substituted amine, aniline or arylalcohol using a Pd catalyst under appropriate reaction conditions known to one of skill in the art. It is noted that the foregoing discussions relating to the carbene or phosphine ligands, bases, solvents and palladium catalysts are set forth with the methods for the preparing the compounds of Formula I via solid-support are fully applicable to the methods for preparing the compounds of Formula I via solution phase, and, thus, they will not be repeated here.

IV. Methods for Inducing Cell Dedifferentiation

The compositions of the present invention can conveniently be used in methods for inducing dedifferentiation of mammalian cells. A mammalian cell is contacted with a compound of Formula I (or a composition thereof), whereupon the mammalian cell dedifferentiates into a multipotent stem cell.

1. Suitable Cells

Suitable lineage committed mammalian cells can be any lineage committed cell type (e.g., myoblasts or osteoblasts) and can be derived from any suitable mammal (e.g., rodents such as, for example, mice, rats, guinea pigs, and rabbits; non-rodent mammals such as, for example, dogs, cats, pigs, sheep, horses, cows, and goats; primates such as, for example, chimpanzees and humans). The lineage committed cells may be primary cells or may be cells maintained in culture. If the cells are maintained in culture, they are typically contacted with the compounds/compositions of the present invention between the 12th and 15th passage in culture. Methods for isolation and culture of human and mammalian cells are well known in the art and have been described in, e.g., Humason, Animal Tissue Techniques, $4^{th}$ ed., W. H. Freeman and Company (1979); Freshney et al., CULTURE OF ANIMAL CELLS (3rd ed. 1994); and Ricciardelli et al., (1989) *In Vitro Cell Dev. Biol.* 25: 1016.

2. General Culturing Methods

The mammalian cells may be contacted with a compound of Formula I, such as Compound A, alone or with a compound of Formula I, such as Compound A, in the presence of growth factors (e.g., fibroblast growth factor or TGF-β),. Those of skill in the art will appreciate that the amount of a compound of Formula I, such as Compound A, and growth factors can be adjusted to facilitate dedifferentiation of particular lineage committed cell types. Typically, the amount of Compound A contacted with the cells is from about 0.1 μM (52 ng/ml) to about 50 μM (2.6 μg/ml), more typically from about 0.25 μM to about 35 μM, even more typically from about 0.5 μM to about 25 μM, yet more typically from about 0.75 μM to about 15 μM, most typically at about 5 μM.

This aspect of the present invention relies upon routine techniques in the field of cell culture. Suitable cell culture methods and conditions can be determined by those of skill in the art using known methodology (see, e.g., Freshney et al., 1994, supra). In general, the cell culture environment includes consideration of such factors as the substrate for cell growth, cell density and cell contract, the gas phase, the medium, and temperature.

Incubation of cells is generally performed under conditions known to be optimal for cell growth. Such conditions may include, for example, a temperature of approximately 37° C. and a humidified atmosphere containing approximately 5% $CO_2$. The duration of the incubation can vary widely, depending on the desired results. In general, incubation is preferably continued until the cells express suitable Proliferation is conveniently determined using $^3$H thymidine incorporation or BrdU labeling.

Plastic dishes, flasks, or roller bottles may be used to culture cells according to the methods of the present invention. Suitable culture vessels include, for example, multi-well plates, petri dishes, tissue culture tubes, flasks, roller bottles, and the like.

Cells are grown at optimal densities that are determined empirically based on the cell type. Cells are typically passaged 12-15 times and discarded after 15 passages.

Cultured cells are normally grown in an incubator that provides a suitable temperature, e.g., the body temperature of the animal from which is the cells were obtained, accounting for regional variations in temperature. Generally, 37° C. is the preferred temperature for cell culture. Most incubators are humidified to approximately atmospheric conditions.

Important constituents of the gas phase are oxygen and carbon dioxide. Typically, atmospheric oxygen tensions are used for cell cultures. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of 1-10% in the incubator. The preferred $CO_2$ concentration typically is 5%.

Defined cell media are available as packaged, premixed powders or presterilized solutions. Examples of commonly used media include MEM-α, DME, RPMI 1640, DMEM, Iscove's complete media, or McCoy's Medium (see, e.g., GibcoBRL/Life Technologies Catalogue and Reference Guide; Sigma Catalogue). Typically, MEM-α or DMEM are used in the methods of the invention. Defined cell culture media are often supplemented with 5-20% serum, typically heat inactivated serum, e.g., human, horse, calf, and fetal bovine serum. Typically, 10% fetal bovine serum is used in the methods of the invention. The culture medium is usually buffered to maintain the cells at a pH preferably from about 7.2 to about 7.4. Other supplements to the media typically include, e.g., antibiotics, amino acids, and sugars, and growth factors.

B. Methods of Differentiating Dedifferentiated Lineage Committed Cells

One aspect of the present invention provides methods for differentiating the multipotent stem cells derived from lineage committed cells. In an exemplary embodiment, lineage committed cells (e.g., myoblasts) are contacted with-a composition comprising Compound A and induced to dedifferentiate into multipotent stem cells (e.g., mesenchymal stem cells). The multipotent stem cells are then induced to differentiate into lineage committed cells. In the case of multipotent mesenchymal stem cells, they are cultured under conditions conducive to inducing differentiation into any one of several cell types including, e.g., osteoblasts, myoblasts and myotubes, and chondrocytes Methods and culture media for differentiating multipotent stem cells into lineage committed cells are well known to those of skill in the art and are described in, e.g., U.S. Pat. Nos. 6,617,159; 5,635,386; and 5,397,706.

Differentiation of the multipotent stem cells into differentiated cells can be detected by any means known in the art including, e.g., detecting expression of cell type-specific transcription factors, detecting expression of cell type-specific proteins, and detecting morphological changes in the cells. For example, osteoblasts typically express the following proteins: alkaline phosphatase (ALP), collagen type I, osteocalcin, and osteoponin; and the following transcription factors: Cbfa1/Runx2, gsc, Dlx1, Dlx5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, *Annu. Rev. Cell. Dev. Biol.* 16:191 (2000)). As a further example, myoblasts typically express the following proteins: MyoD, Myf5, myosin, CD56 and desmin.

1. Detection of Cell-Specific Proteins

Expression of cell-specific proteins may be detected by measuring the level of the cell-specific protein or mRNA. One of skill in the art will appreciate that the particular method used to detected the cell-specific protein or mRNA is not a critical part of the present invention. Methods of detecting cell-specific proteins and mRNA are well known in the art. For example, the level of particular cell-specific proteins can conveniently be measured using immunoassays such as immunohistochemical staining, western blotting, ELISA and the like with an antibody that selectively binds to the particular cell specific proteins or a fragment thereof. Detection of the protein using protein-specific antibodies in immunoassays is known to those of skill in the art (see, e.g., Harlow & Lane, Antibodies: A Laboratory Manual (1988), Coligan, Current Protocols in Immunology (1991); Goding, Monoclonal Antibodies: Principles and Practice (2d ed. 1986); and Kohler & Milstein, Nature 256:495-497 (1975). For measurement of mRNA, amplification, e.g., PCR, LCR, or hybridization assays, e.g., northern hybridization, RNAse protection, dot blotting, are preferred. The level of protein or mRNA is detected, for example, using directly or indirectly labeled detection agents, e.g., fluorescently or radioactively labeled nucleic acids, radioactively or enzymatically labeled antibodies. These assays are well-known to those of skill in the art and described in, e.g., Ausubel, et al. ed. Current Protocols in Molecular Biology (2001). In the case of cell-specific enzymes, measurement of enzymatic activity (e.g., alkaline phosphatase) can be used as an indicia of cellular differentiation. Methods of measuring cellular enzymes are well known in the art and are described in, e.g., (see, e.g., Harlow & Lane, 1988, supra; Coligan, 1991, supra; Goding, 1986, supra; and Kohler & Milstein, 1975, supra).

2. Detection of Cell-Specific Transcription Factors

Expression of cell-specific transcription factors can be detected using reporter gene assays. These assays are well known to those of skill in the art and are described in, e.g., Ausebel et al., supra. and U.S. Patent Application No. 60/418,898. For example, expression of the bone specific transcription factor Cbfa1/Runx2 can be to detect osteogenesis; expression of the chondrocyte specific transcription factors p38 MAPK or c-Maf can be used to detect chondrogenesis; and expression of the myoblast specific transcription factors Mirk (minibrain-related kinase)/dyrk1B or FoxO1 can be used to detect myogenesis.

Reporter genes such as, for example, chloramphenicol acctyltransferase, firefly luciferase, bacterial luciferase or β-galactosidase can be used in the reporter gene assays. The reporter construct is typically transiently or stably transfected into a cell. The promoter region of the relevant gene is typically amplified by PCR appropriate primers. The resulting PCR product is inserted into a suitable cloning vector, amplified and sequenced. The resulting plasmid is digested with appropriate restriction enzymes and the resulting fragment is inserted into a vector comprising a reporter gene.

For reporter gene assays with transiently transfected cells, the cells are typically seeded in a 6-well plate at a density of 30,000 cells/well in 2 mL of growth medium an incubated overnight or for a suitable time. Plasmid DNA is transfected into the cells using a suitable transfection reagent. After 8 hours, the transfected cells are plated into 96-well assay plates (e.g., Corning) and treated with an appropriate amount of a compound of Formula I (e.g., Compound A). The cells are incubated for 4 days, then the reporter gene activity in the cells is assayed using methods known to those of skill in the art.

For reporter gene assays with stably transfected cells, the cells are typically seeded in a 6-well plate at a density of 30,000 cells/well in 2 mL of growth medium an incubated overnight or for a suitable time. An appropriate amount of reporter plasmid and a vector comprising a selectable marker (e.g., an antibiotic resistance gene) are co-transfected into the cells using an appropriate transfection reagent. After an appropriate incubation time, cells are seeded in a 10 cm culture dish and an appropriate amount of antibiotic is added to the culture medium. Fresh antibiotic is added at appropriate intervals. The antibiotic resistant colonies are pooled to yield the stably transfected cells. The transfected cells are plated into 96-well assay plates (e.g., Corning) and treated with an appropriate amount of a compound of Formula I (e.g., Compound A). The cells are incubated for 4 days, then the reporter gene activity in the cells is assayed using methods known to those of skill in the art.

3. Detection of Morphological Changes

Morphological changes in cells are also indicia of cell differentiation and can be detected using any means known to those of skill in the art. Typically, differentiated cells are stained with a suitable dye and morphological changes are visually detected, e.g., using a microscope. For example, differentiated cells can be stained with Oil Red O, which identifies the presence of liquid droplets within the cytoplasmic membrane characteristic of adipocytes. Methods and compositions for staining cells to identify particular cell types are well known in the art and are described in, e.g., Albertine and Gee, *J. Leuk. Biol.* 59(5):631-8 (1996); Allsopp et al., *J. Immunol. Methods* 1998 May; 214(1-2):175-86 (1998); Ashley et al., *Leuk. Res.* 18(1):37-48 (1994); Ashley et al., *Leuk. Res.* 17(10):873-82 (1993);. Boutonnat et al., *C. R. Acad. Sci. III* 321(11):901-7(1998); Boyd *Cell Growth Differ.* 4(9):777-84 (1993); Dell'Accio et al., *J. Orthop. Res.* 21(1):123-31 (2003); Ford et al., *J. Surg. Res.* 62(1):23-8 (1996); Haas et al., *Acta Histochem.* 102 (3 ):273-80 (2000); Horan et al., *Methods Cell Biol.* 33:469-90 (1990); Khalaf et al., *J. Immunol. Methods* 165(1):121-5 (1993); Melnicoff et al., *J. Leuk. Biol.* 43(5):387-97 (1988); Modo et al., *Neuroimage* 17(2):803-11 (2002); Muirhead, *Morphologie* 85:27(2001); Parish, *Immunol. Cell Biol.* 77(6):499-508 (1999); Pierelli et al., *Methods Cell Biol.* 64(1):153-70 (2001); Waters et al., *Cytometry* 48(3):146-52 (2002); Yuan et al., *Microvascular Res.* 40:228-9 (1990); and U.S. Pat. Nos.: 6,387,326; 6,076,583; 5,700,346; 5,318,795; 4,792,521; 4,783,401; 4,762,701; and 4,859,584.

V. Methods of Screening

One embodiment of the invention provides a method of screening for additional compounds that induce dedifferentiation of a lineage committed cell. A lineage committed mammalian cell is contacted with a test compound suspected of inducing dedifferentiation of lineage committed mammalian cells. Dedifferentiation of the lineage committed cells can be detected by detecting loss of cell-specific proteins and cell-specific transcription factors as described above. To determine whether the lineage committed cells have dedifferentiated into multipotent stem cells, the dedifferentiated cells are cultured in at least two separate cell culture media, each of which induces differentiation of stem cells into different cell types. Assays to determine whether the dedifferentiated cells have undergone differentiation into the first or second cell type are conduction; and induction of differentiation of the stem cells into cell types identifies the test compound as a compound that induces dedifferentiation of lineage committed mammalian cells.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. Millions of chemical compounds can be synthesized through such combinatorial mixing of chemical building blocks (Gallop et al., *J. Med, Chem.* 37(9):1233-1251 (1994)).

Preparation and screening of combinatorial chemical libraries is well known to those of skill in the art. Such combinatorial chemical libraries include, but are not limited to, substituted purines, pyrimidines, quinazolines, pyrazines, pyrrolopyrimidine, pyrazolopyrimidine, phthalazines, pyridazines, and quinoxalines (see, e.g., Ding et al., *J. Am. Chem. Soc.* 124:1594 (2002);Gray et al., *Science* 281:533 (1998); Rosania et al. *Nat. Biotechnol.* 18:304 (2000); and Rosania et al., *Proc. Natl. Acad. Sci. USA.* 96:4797 (1999); peptide libraries (see, e.g., U.S. Pat. No. 5,010,175, Furka, *Pept. Prot. Res.* 37:487-493 (1991), Houghton et al., *Nature,* 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with a Beta-D-Glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho, et al., *Science* 261:1303 (1993)), and/or peptidyl phosphonates (Campbell et al., *J. Org. Chem.* 59:658 (1994)). See, generally, Gordon et al., *J. Med. Chem.* 37:1385 (1994), carbohydrate libraries (see, e.g., Liang et al., *Science* 274:1520-1522 (1996), and U.S. Pat. No. 5,593,853), and small organic molecule libraries (see, e.g., benzodiazepines, Baum, C&EN, January 18, page 33 (1993); isoprenoids, U.S. Pat. No. 5,569, 588; thiazolidinones and metathiazanones, U.S. Pat. No. 5,549,974; pyrrolidines, U.S. Pat. Nos. 5,525,735 and 5,519, 134; morpholino compounds, U.S. Pat. No. 5,506,337; benzodiazepines, U.S. Pat. No. 5,288,514, compounds that regulate adenyl cyclase and cyclic AMP, such as, for example, forskolin and its derivatives, U.S. Pat. Nos. 5,789,439; 5,350, 864, and 4,954,642.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. The above devices, with appropriate modification, are suitable for use with the present invention. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow,. RU, 3D Pharmaceuticals, Exton, Pa., Martek Biosciences, Columbia, Md., etc.).

The assays to identify compounds that induce dedifferentiation of lineage commited cells are amenable to high throughput screening. High throughput assays for evaluating the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate procedures, including sample and reagent pipeting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

VI. Methods of Treatment

Another embodiment of the invention provides methods of treating individuals with diseases or disorders which can be treated by administration of differentiated cells. In this embodiment, a lineage mammalian cell is contacted with a compound of Formula I (e.g., Compound A or a composition thereof), whereupon the mammalian cell dedifferentiates into a multipotent stem cell. The multipotent stem cell can then be cultured under conditions suitable for inducing differentiation of the stem cells into a differentiated cell of a desired lineage (e.g., a cell of an osteoblast lineage, a cell of a chondrocyte lineage, or a cell of an adipocyte lineage). The differentiated cell is then administered to an individual in need of such treatment. Lineage committed cells can be extracted from the subject to be treated, i.e., autologous (thereby avoiding immune-based rejection of the differentiated cells), or can be from a second subject, i.e., heterologous. In either case, administration of cells can be combined with an appropriate immunosuppressive treatment.

1. Administration of Differentiated Cells

Differentiated cells can be administered to a subject by any means known to those of skill in the art. In an exemplary embodiment of the invention, differentiated osteoblast cells on an intact solid support (e.g., a three-dimensional matrix or a planar surface) can be administered to the subject, e.g., via surgical implantation. Alternatively, the differentiated osteoblast cells can be detached from the matrix, i.e., by treatment with a protease, before administration to the subject, e.g., intravenous, subcutaneous, or intraperitoneal.

The cells may be in formulations suitable for administration, such as, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can be prepared from sterile powders, granules, and tablets.

For surgical implantation, differentiated cells are typically left on an intact solid support, e.g., a three-dimensional matrix or planar surface. The matrix or planar surface is surgically implanted into the appropriate site in a subject. For example, a patient needing a bone graft can have differentiated cells on an intact solid support surgically implanted.

In determining the effective amount of the cells to be administered in the treatment or prophylaxis of conditions owing to diminished or aberrant differentiated cells, the physician evaluates cell toxicity, transplantation reactions, progression of the disease, and the production of anti-cell antibodies. For example, osteoblast cells differentiated according to the methods of the present invention can be administered in an amount effective to provide osteoblasts to the subject, taking into account the side-effects of the osteoblasts at various concentrations, as applied to the mass and overall health of the patient. Administration can be accomplished via single or divided doses.

One of skill in the art will appreciate that the differentiated cells can be used alone or in combination with other compounds and therapeutic regimens to induce tissue regeneration (e.g., osteogenesis). In an exemplary embodiment, the stem cells may be induced to differentiate into osteoblasts which can be administered to a patient in conjunction with bone morphogenetic proteins (e.g., BMP-2, BMP-4, and BMP-7) or anti-resorptive medications (e.g., bisphosphonates such as, for example, alendronate sodium and risedronate sodium; hormones, such as, for example, calcitonin and estrogens, and selective estrogen receptor modulators, such as, for example, raloxifene) that affect bone remodeling cycle. To assess the effect of the administration of osteoblasts on bone density, a baseline measurement of bone density in an individual who will receive treatment may taken. Bone density is periodically measured at suitable intervals during and after administration of the compounds of Formula I, e.g., Compound A. Methods and devices for measuring bone density are well known in the art and are described in, e.g., U.S. Pat. Nos. 6,436,042; 6,405,068; 6,320,931; 6,302,582; 6,246,745; 6,230,036; 6,213,934; 6,102,567; 6,058,157; 5,898,753; 5,891,033; 5,852,647; 5,817,020; 5,782,763; 5,778,045; 5,749,363; 5,745,544; 5,715,820; 5,712,892; 5,572,998; and 5,480,439.

EXAMPLES

The following examples are offered to illustrate, but not to limit, the claimed invention.

Example 1

Synthesis and Characterization of Compound A

The phosphine ligand for the Pd-catalyzed coupling was purchased from Strem Chemicals. All the other chemicals were purchased from Aldrich.

Solution Phase Synthesis of 2-(4-morpholinoanilino)-6-cyclohexylpurine (Compound A)

2-(4-Morpholinoanilino)-6-cyclohexylamino-purine (i.e., reversine or Compound A) was synthesized using the methods similar to those previously described in Ding et al., *J. Am. Chem. Soc.* 124:1594 (2002). To a solution of 2-fluoro-6-chloropurine (87 mg, 0.5 mmol) in n-butanol (5 mL) was added cyclohexylamine (58 μL, 0.5 mmol) and diisopropylethylamine (100 μL, 0.6 mmol). The mixture was heated to 80° C. with vigorous stirring for 12 hours. The solvent was then removed under reduced pressure and the crude was used directly in the next step reaction without further purification. The crude 2-fluoro-6-cyclohexylamino-purine (0.5 mmol) was dissolved in ethanol (1 mL), followed by addition of 4-morpholinoaniline (178 mg, 1.0 mmol). The mixture was heated to 75° C. in a sealed tube with vigorous stirring for 24 hours. The solvent was then removed under reduced pressure and the crude material was directly purified by flash chromatography to afford 2-(4-morpholinoanilino)-6-cyclohexylamino-purine as a pale white solid (130 mg, overall 67% yield). $^1$H NMR (500 MHz, DMSO-d6) δ 1.14-1.24 (m, 1H), 1.26-1.39 (m, 4H), 1.59-1.67 (m, 1H), 1.73-1.81 (m, 2H), 1.94-1.99 (m, 2H), 3.07 (dd, J=4.8, 4.7 Hz, 4H), 3.74 (dd, J=4.8, 4.7 Hz, 4H), 3.90-4.06 (m, 2H), 6.93 (d, J=9.1 Hz, 2H), 7.51 (d, J=8.8 Hz, 2H), 8.31 (s, 1H), 8.38 (br. s, 1H), 9.68 (br. s, 1H); $^{13}$C NMR (125 MHz, $CD_3OD$) δ 26.1, 26.5, 33.4, 40.4, 52.1, 67.4, 116.5, 118.6, 124.9, 133.2, 141.8, 147.9, 148.6, 152.9, 153.3; MALDI-FTMS for $C_{21}H_{28}N_7O$ ($MH^+$): calcd 394.2350. Found 394.2341.

Example 2

Materials and Methods

Cell culture and small molecule screen. C2C12 cells (ATCC CRL-1772) are cultured in DMEM (Gibco) supplemented with 10% fetal bovine serum (HyClone) at 37° C. in 5% $CO_2$. The murine C2C12 cell is a myogenic lineage committed myoblast. Upon withdrawal of serum, confluent C2C12 cells can differentiate and fuse into characteristic multi-nucleated myotubes.

For the small molecule screen, proliferating C2C12 cells are plated into black 384-well tissue culture plates (Greiner) at a density of 1,000 cells/well in DMEM with 10% FBS. Test compounds (i.e., small molecules) are added at a final concentration of 5 μM after 16 hours (i.e., the time point when cells typically attach to the bottom of a tissue culture plate).

After the cells are treated with test compounds for four days, the test compound is removed and the cell culture medium is changed to osteogenic differentiation medium (ODM) containing 50 μg/ml ascorbic acid 2-phosphate, 0.1 μM dexamethasone and 10 mM β-glycerophosphate. Cell culture medium is typically changed every two days. After seven additional days of culture in ODM, the ODM is removed and cells are lysed by incubation in 10 μL passive lysis buffer (Promega) for 10 min, followed by addition of 10 μL alkaline phosphatase substrate solution (AttoPhos, Promega). After a 15 minute room temperature incubation, fluorescence intensity is read on an Acquest (Molecular Devices) as directed by the manufacturer.

Osteogenesis Assays. Mammalian cells (e.g., C2C12 myoblast cells) are treated with a suitable amount of a test compound (e.g. 5 μM reversine) in DMEM supplemented with 10% FBS for four days. The compound is then removed and medium is changed to ODM every two days. After seven days following induction of osteogenesis, the cells are washed with PBS (200 μL, 3 times) and fixed with 10% formalin solution (Sigma) for 20 min. The fixed cells are then washed with PBS (200 μL, 3 times) and stained with the Alkaline Phosphatase Staining Kit 86R (Sigma) as directed by the manufacturer. Images are taken on a Nikon Eclipse TE2000 microscope at 200 fold magnification.

Adipogenesis Assays: Mammalian cells (e.g., C2C12 myoblast cells) were treated with a suitable amount of a test compound (e.g., 5 μM reversine) in DMEM supplemented with 10% FBS for four days. The compound was then removed and medium was changed to adipogenic differentiation medium (ADM) containing 0.5 mM 3-isobutyl-1-methylxanthine, 2.5 μg/ml insulin, and 0.5 μM dexamethasone. Typically, the ADM is replaced every two days. After seven days following induction of adipogenesis, the cells are washed with PBS (200 μL, 3 times) and fixed with 10% formalin solution (Sigma) for 10 min. The fixed cells are then washed with PBS (200 μL, 3 times) and stained with the 0.7% Oil Red O (Sigma) as directed by the manufacturer. Images are taken on a Nikon Eclipse TE2000 microscope at 200 fold magnification.

Example 3

Identification of Compound A as a Compound with Cell Dedifferentiation Inducing Activity A heterocycle combinatorial library of approximately 50,000 compounds designed around a large number of kinase-directed scaffolds were screened, including substituted purines, pyrimidines, quinazolines, pyrazines, pyrrolopyrimidine, pyrazolopyrimidine, phthalazines, pyridazines, and quinoxalines was screened to identify small molecules with dedifferentiation inducing activity (see, e.g., Ding et al., *J. Am. Chem. Soc.* 124:1594(2002);Gray et al., *Science* 281: 533 (1998); Rosania et al. *Nat. Biotechnol.* 18:304 (2000); and Rosania et al., *Proc. Natl. Acad. Sci. USA.* 96:4797 (1999).

To identify molecules that induce dedifferentiation of mammalian cells, an assay was devised, based on the notion that lineage-reversed myoblasts should regain multipotency, i.e., they should acquire the ability to differentiate into multiple non-permitted cell lineages when exposed to conditions that typically induce differentiation of multipotent mesenchymal progenitor cells into adipocyptes, osteoblasts or chondrocytes. Osteoblast formation was chosen for the primary screen since there are established osteogenic inducing conditions and a high throughput assay for detecting the bone specific marker, alkaline phosphatase (ALP or ALK (see e.g., Wu et al., *J. Am. Chem. Soc.* 124:14520-14521 (2002)).

A two stage screening protocol was used. C2C12 myoblast cells were initially treated with the small molecules for four days to induce dedifferentiation, and then assayed for their ability to undergo osteogenesis upon addition of known osteogenic inducing agents. To carry out the screen, C2C12 cells were plated in 384-well plates in growth medium (DMEM with 10% fetal bovine serum) and after overnight incubation (during which time cells attach to the bottom of the plate) 5 μM of compound was added. After four days, compound was removed and the medium was changed to osteogenic inducing medium (see, e.g., Ding et al., *J. Am. Chem. Soc.* 124:1594-1596 (2002) containing 50 μg/ml ascorbic acid 2-phosphate, 0.1 μM dexamethasone and 10 mM β-glycerophosphate. The culture was maintained for an additional seven days, cells were lysed and then assayed for ALP activity using the fluorogenic substrate 2'-[2'-benzothiazoyl]-6'-hydroxybenzothiazole phosphate (BBTP).

Figure 2:
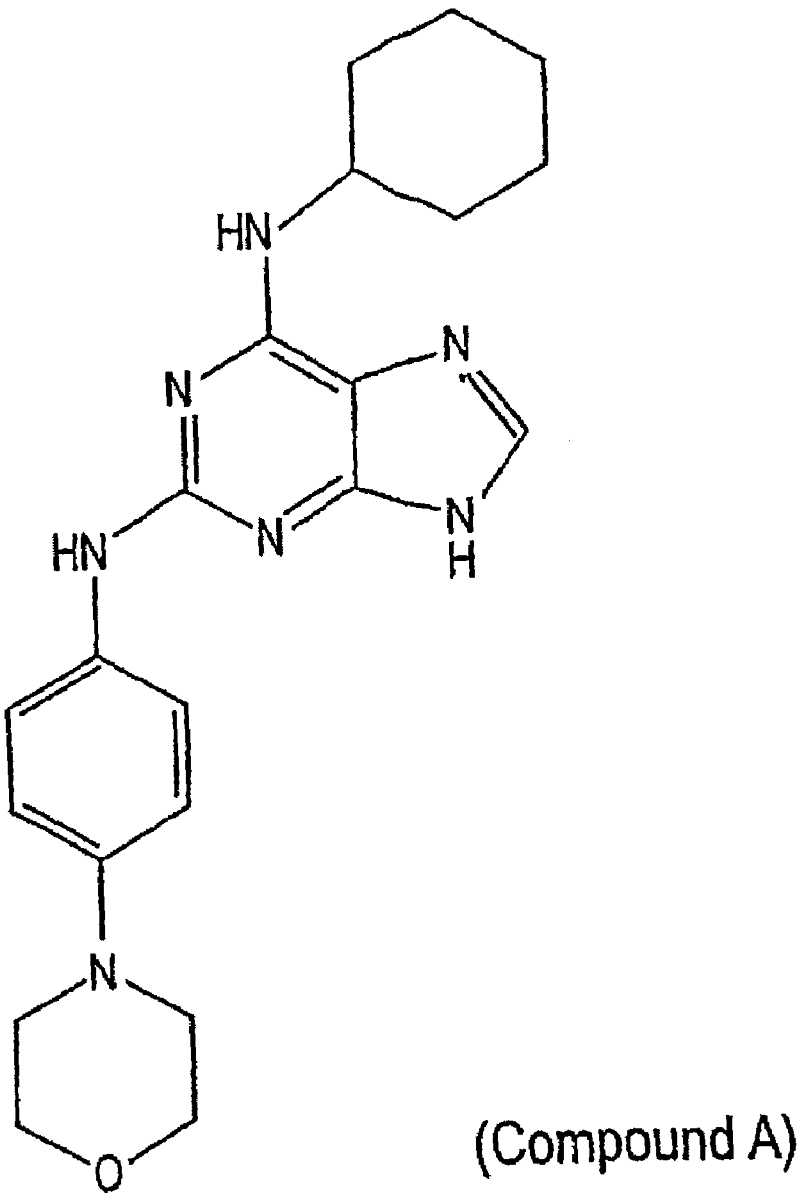
FIG. 2 illustrates the structure of Compound A.

Among a series of 2,6-disubstituted purine analogs identified in the primary screen, a 2-(4-morpholinoanilino)-6-cyclohexylamino-purine analog (i.e., Compound A or reversine, FIG. 2) was found to induce the highest level (7 fold) of ALP activity relative to the DMSO control treatment. On day four of compound treatment, striking differences were observed between the reversine treated and untreated cells. In the control cells (treated only with DMSO), multi-nucleated myotubes were formed throughout the culture. In contrast, myotube formation was completely inhibited in the presence of 5 μM reversine and cells continued to grow to form a confluent culture of mononucleated cells. In addition, myogenic specific markers such as MyoD and myosin began to disappear. These results suggest that reversine is not simply acting as a selective toxin (see, e.g., Grigoriadis et al., *J. Cell Biol.* 106:2139-2151 (1988)).

Example 4

Cells Gain Multipotency Following Treatment with Reversine

To confirm that the results were not due to transdifferentiation of myogenic cells to osteogenic cells, compounds from the primary screen were tested to determine (1) whether they can induce osteogenesis in the absence of the osteogenesis inducing cocktail and (2) whether cells treated with compounds can differentiate into adipocytes under conditions that induce adipogenesis (see, e.g., Jaiswal et al., *J. Cell. Biochem.* 64:295-312 (1997)). After four days of treatment with reversine, the compound was removed and cells were then grown in osteogenic differentiation medium (ODM) or adipogenic differentiation medium (ADM). At the end of day seven, under ODM conditions, 35% of cells stained positive for ALP. Similarly when exposed to ADM condition, 40% of cells had the characteristic fat cell morphology, oil droplets inside the cytoplasmic membrane, and stained positive with Oil Red O. Again, in the control culture, confluent C2C 12 cells continue to form myotubes and were unaffected by the ODM and ADM conditions. These results clearly demonstrate that reversine treated lineage-committed C2C12 myoblasts cells regain multipotency. Moreover, at the effective concentration of reversine (0.5-5 μM), no significant cell death was observed.

In addition, transdifferentiation of C2C12 myoblasts to osteoblasts or adipocytes was not observed under the conditions used to induce osteogenesis or adipogenesis. In the absence of ODM, reversine alone has no osteogenesis activity. Similarly, in the absence of ADM, reversine alone has no adipogenesis activity. These observations confirm that reversine induces dedifferentiation of C2C12 cells rather than trandifferentiation to osteogenic lineage. These observations also that reversine acts as a dedifferentiation inducing agent rather than simply enriching certain type of progenitor cells by selectively killing myoblasts.

Example 5

Clonal analysis of C2C12

Clonal analysis is used to verify that reversine can induce dedifferentiation at the single cell level. C2C12 cells were cultured from a single cell and treated with reversine. After 6 days of treatment, each colony was divided into two portions. One portion was cultured in ODM and another portion was cultured in ADM. The cells were then analyzed using the staining assays described in Example 1. 56 of 97 colonies were determined to be multipotent.

Example 6

Structure-Activity Analysis of Reversine

A preliminary structure-activity relationship (SAR) analysis of the primary screen data revealed that both of the N9-H and the NH substitution at the C2 position of the purine ring are critical (removal of either can completely abolish activity). However, primary amines at the C6 position of the purine ring can be replaced with various hetero-atoms, such as, for example, oxygen and sulfur without loss in activity, suggesting a H-bond donor at this position is not required. Only a limited group of aromatic substituents can be tolerated at the C2 position of the purine ring and an H-bond acceptor is required at the aromatic ring.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of Formula I having the following structure:

I

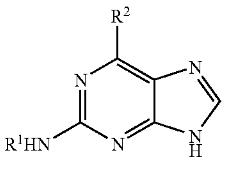

wherein:

$R^1$ is

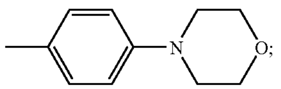

$R^2$ is a member selected from the group consisting of:

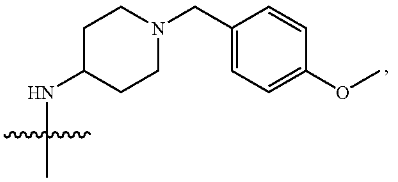

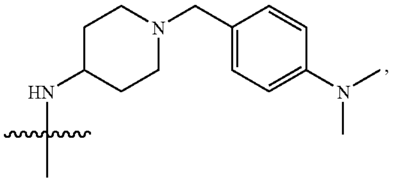

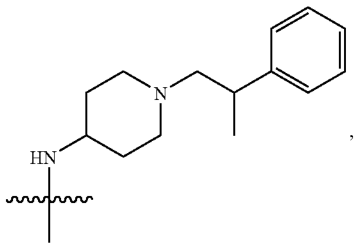

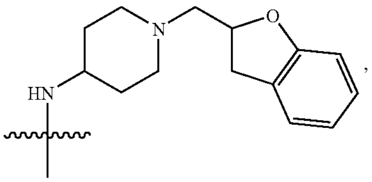

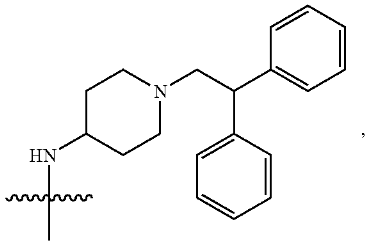

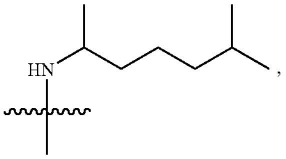

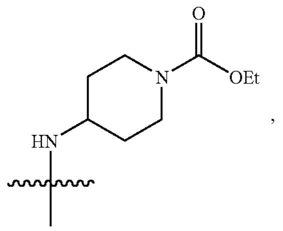

-continued

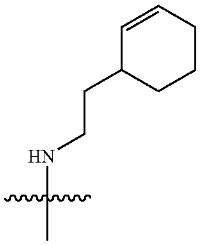

,

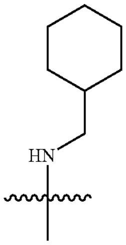

,

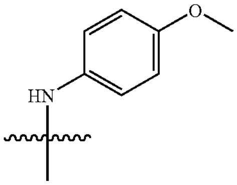

,

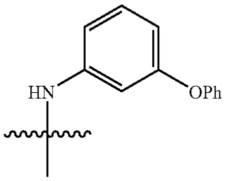

,

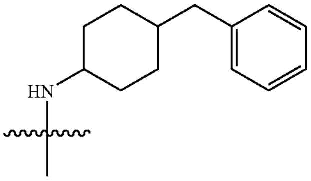

, and

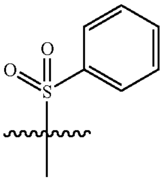

.

2. A pharmaceutical composition comprising a compound of claim 1 and a pharmaceutically acceptable carrier.

3. A method of inducing dedifferentiation of a lineage committed cell, the method comprising:

contacting a lineage committed mammalian cell with a compound of Formula I having the following structure:

I

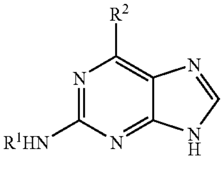

wherein:

$R^1$ is a member selected from a group consisting of

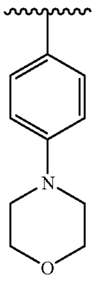

,

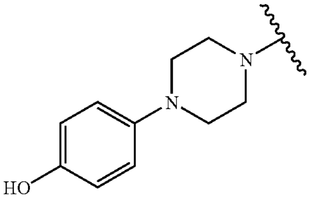

,

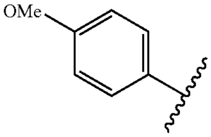

,

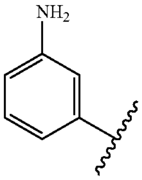

,

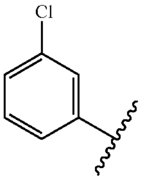

,

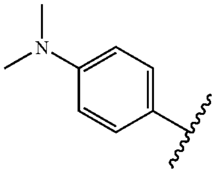

,

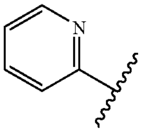

, and

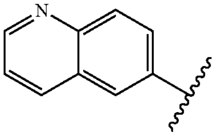

; and $R^2$ is a member selected from the group consisting of

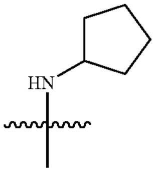

,

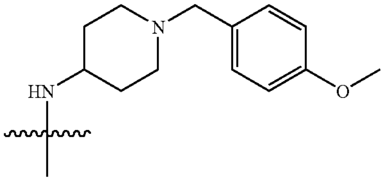

,

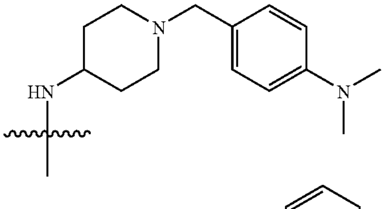

,

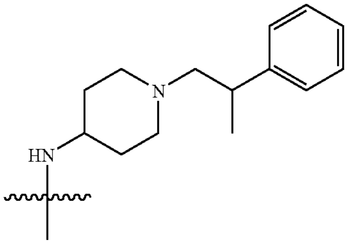

,

-continued

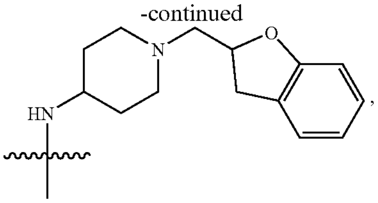
,

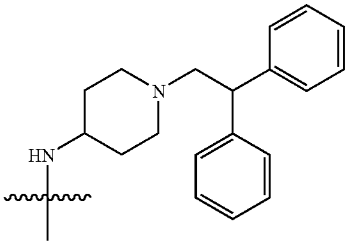
,
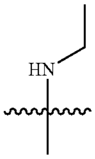
,

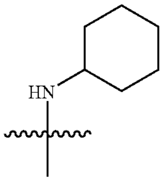
,
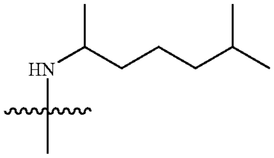
,

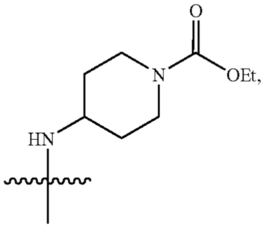
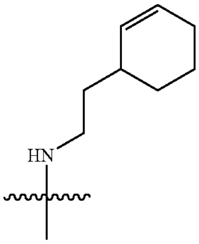
,

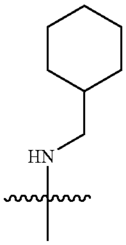
,
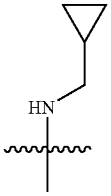
,

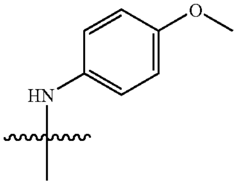
,
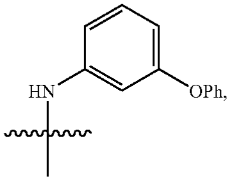

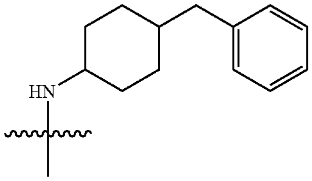
,

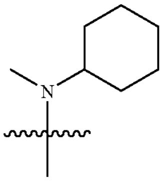
, And
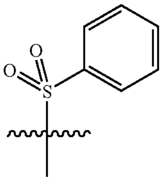
;

whereby the mammalian myoblast cell dedifferentiates into a multipotent progenitor stem cell.

4. The method of claim 3, further comprising detecting dedifferentiation of the mammalian cell into a multipotent progenitor stem cell.

5. The method of claim 4, whereby differentiation of the lineage committed mammalian myoblast cell into a multipotent progenitor stem cell is detected by detecting loss of expression of a marker gene expressed by the lineage committed mammalian cell.

6. The method of claim 5, wherein the marker gene is a member selected from the group consisting of: MyoD, Myf5, myosin, CD56 and desmin.

7. The method of claim 5, wherein the myoblast cell is isolated from a mouse.

8. The method of claim 5, wherein the myoblast cell is isolated from a primate.

9. The method of claim 8, wherein the primate is a human.

10. A method of treating a bone disorder, wherein the bone disorder is associated with defective osteoblasts, the method comprising:

(a) contacting a mammalian cell with a compound of Formula I having the following structure:

I

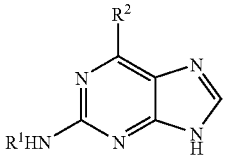

wherein $R^1$ is a member selected from a group consisting of

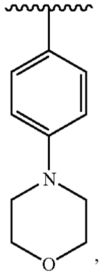
,

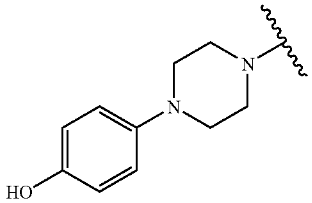
,

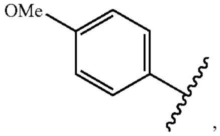
,

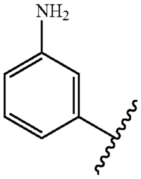
,

-continued
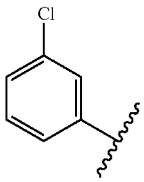
,
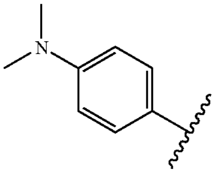
,
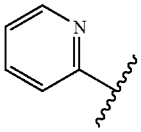
, and
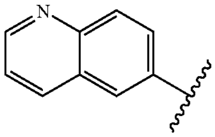
; and
$R^2$ is a member selected from the group consisting of
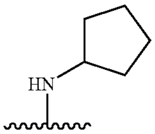
,
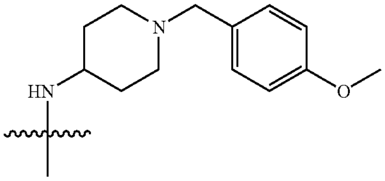
,
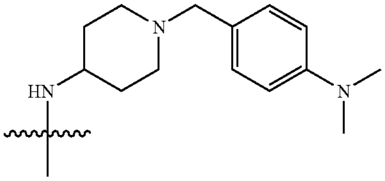
,
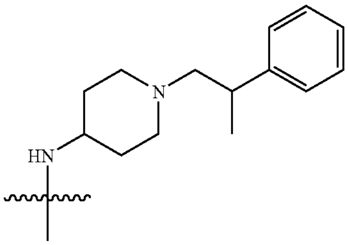
,
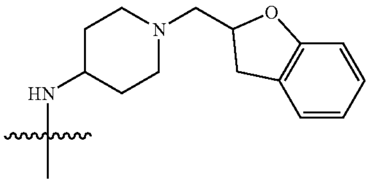
,
-continued
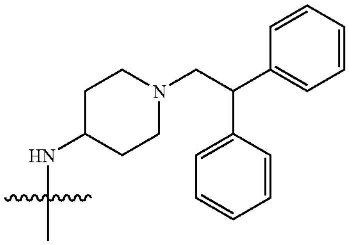
,
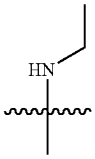
,
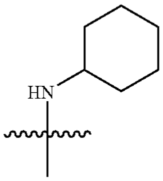
,
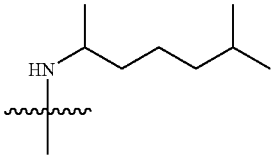
,
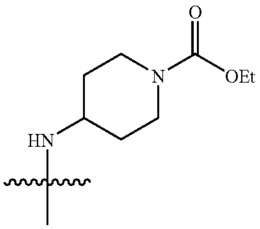
,
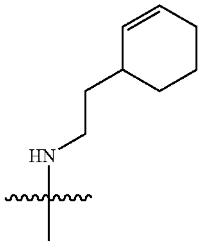
,
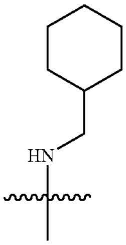
,
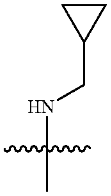
,
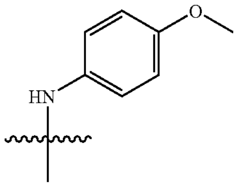
, -continued

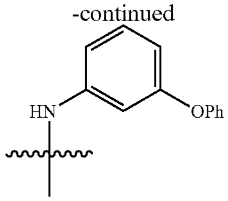

,

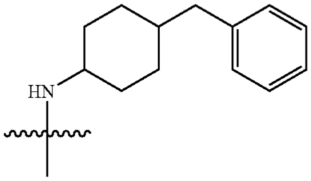

,

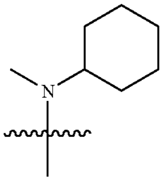

, And

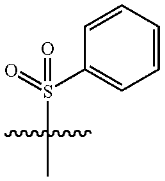

whereby the mammalian cell dedifferentiates into a multipotent stem cell; and (b) contacting the multipotent stem cell with a cell culture medium that induces differentiation of the multipotent stem cell into a cell of an osteoblast lineage; and (c) administering the cell of an osteoblast lineage to an individual with the disorder, thereby treating the disorder.

11. The method of claim 10, wherein the administration is by surgical implantation.

12. The method of claim 10, wherein the mammalian cell is attached to a solid support.

13. The method of claim 10, wherein the bone disorder is osteoporosis.

14. The method of claim 12, wherein the solid support is a three dimensional matrix.

15. The method of claim 12, wherein the solid support is a planar surface.

16. The method of claim 3, wherein said compound is a member selected from the group consisting of:

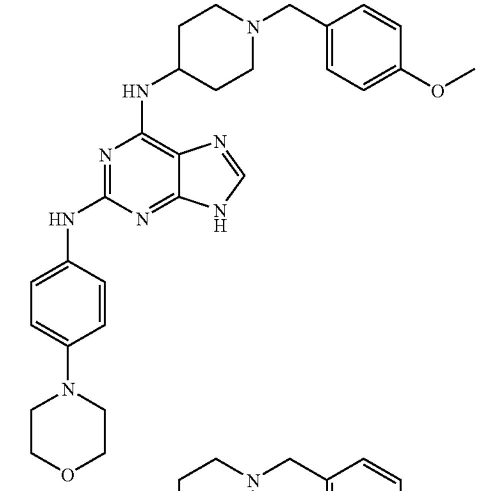

,

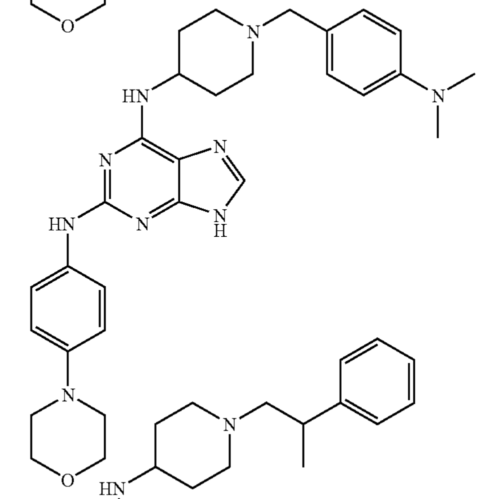

,

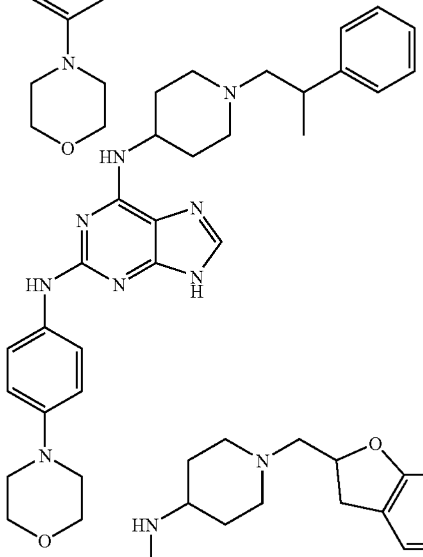

,

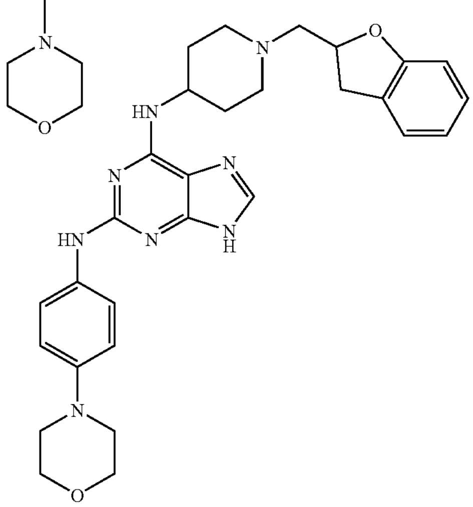

,

-continued
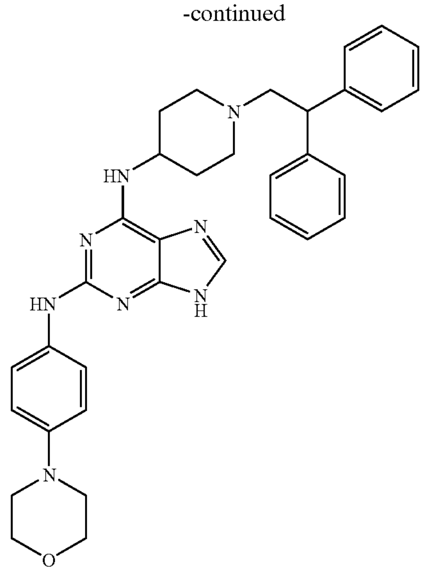
,
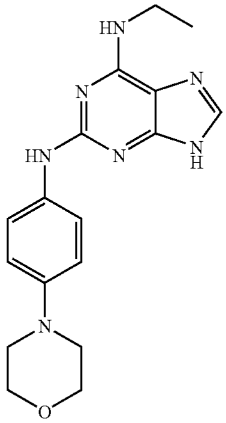
,
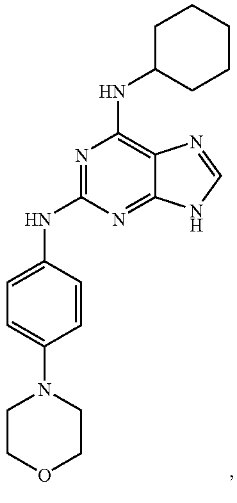
,
-continued
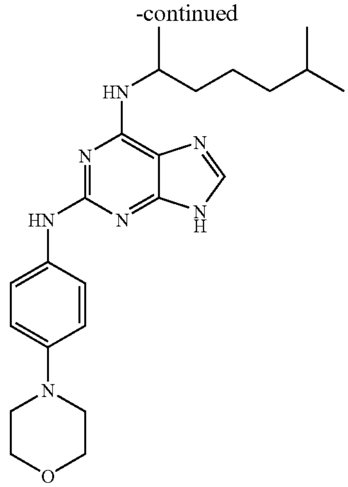
,
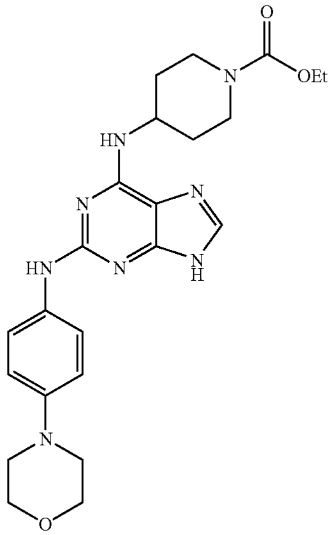
,
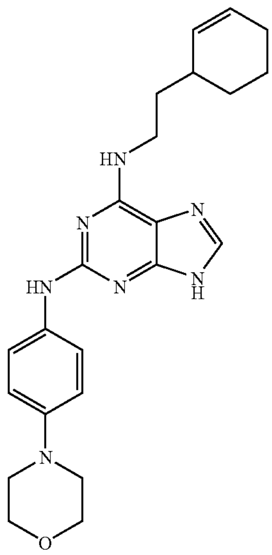
, -continued
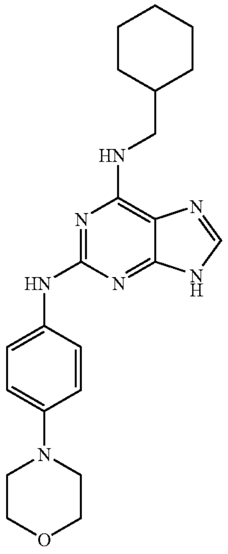
,
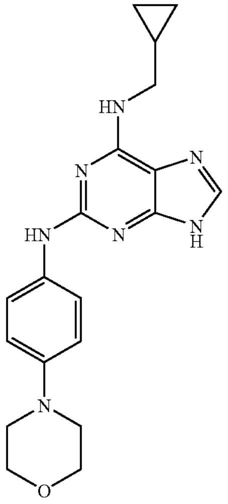
,
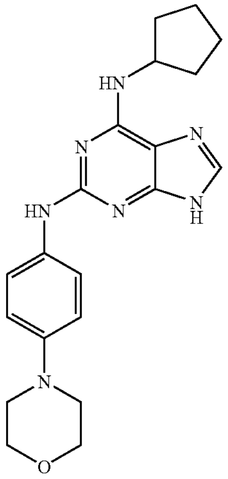
,
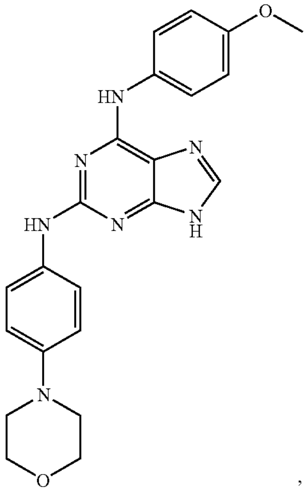
,
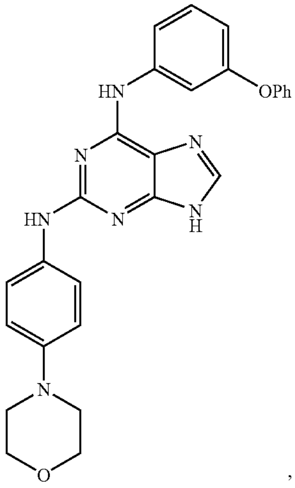
,
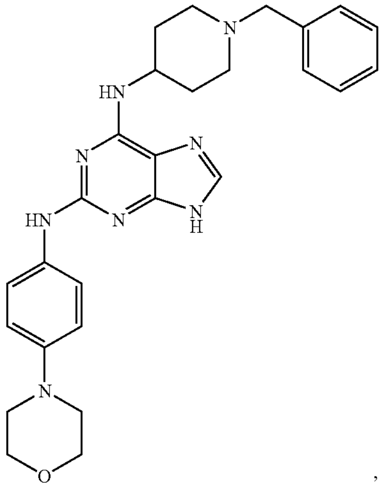
, -continued
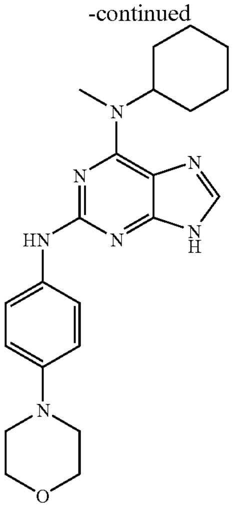
and
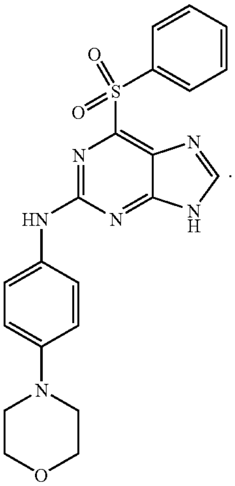
.
17. The method of claim 10, wherein said compound is a member selected from the group consisting of:
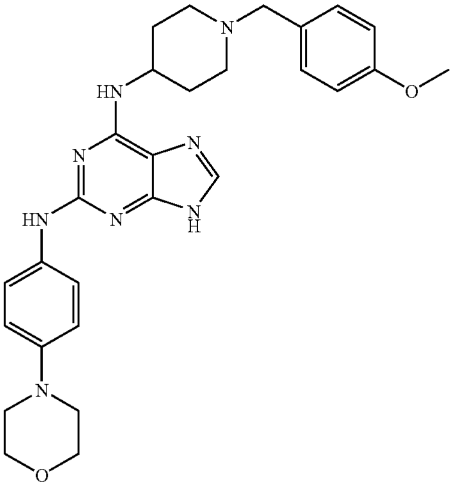
,
-continued
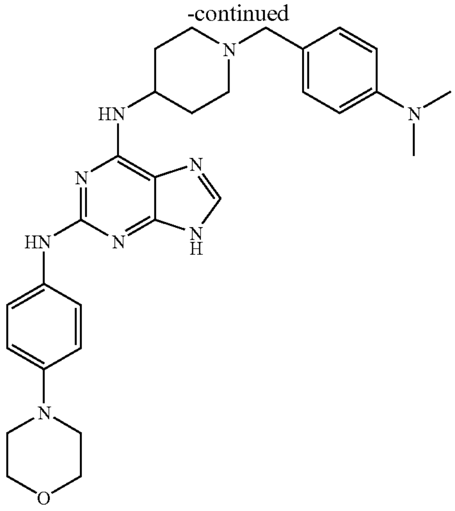
,
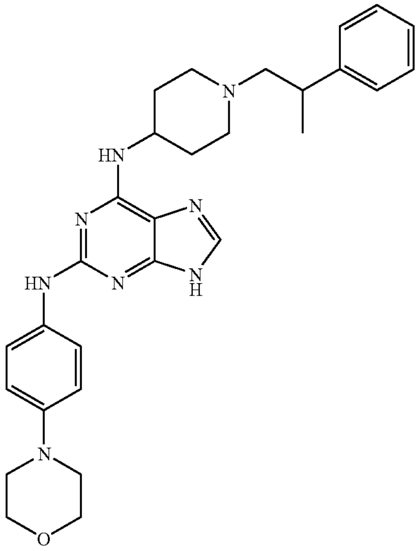
,
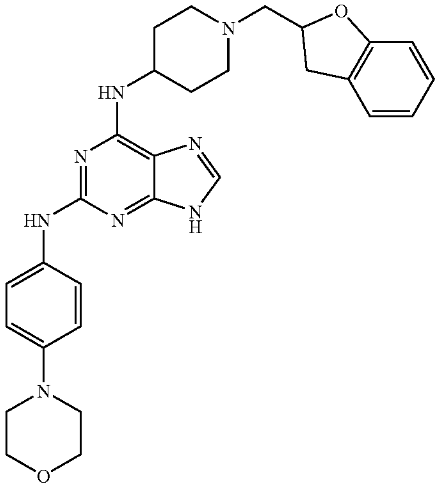
, -continued
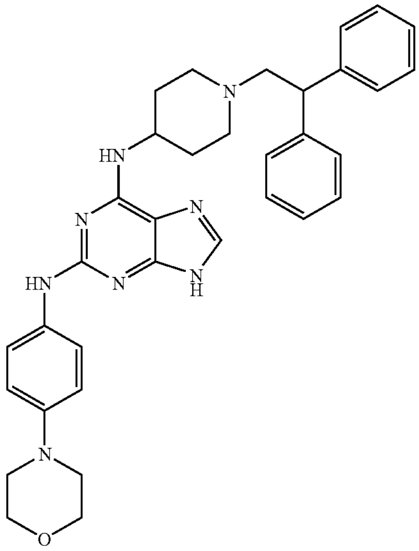
,
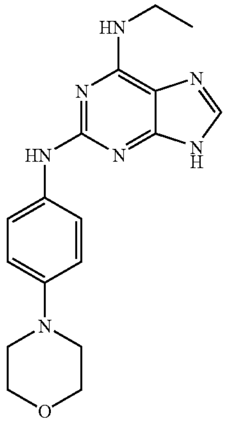
,
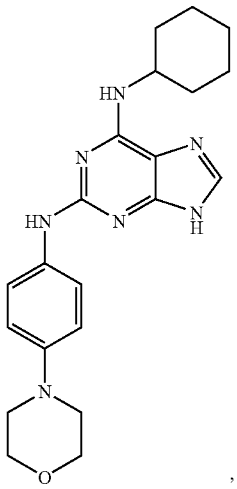
,
-continued
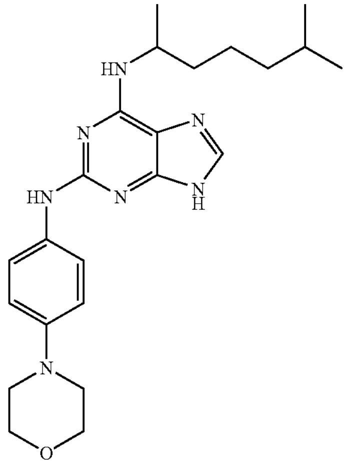
,
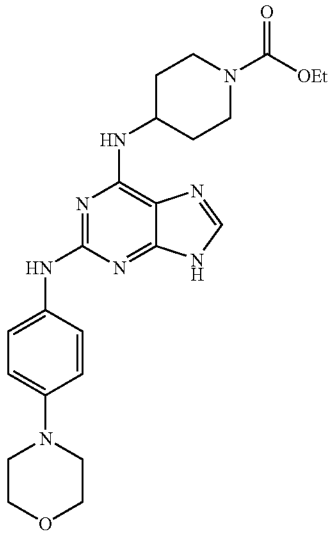
,
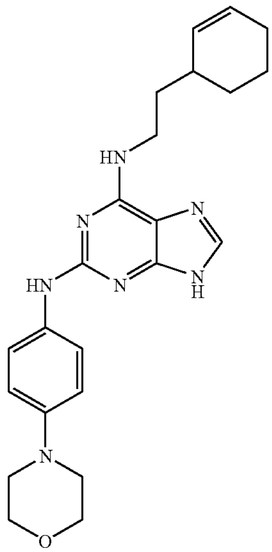
, -continued
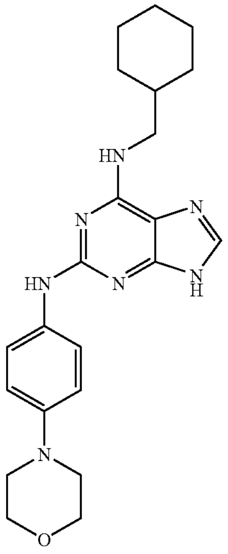
,
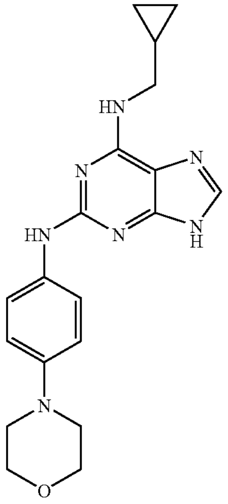
,
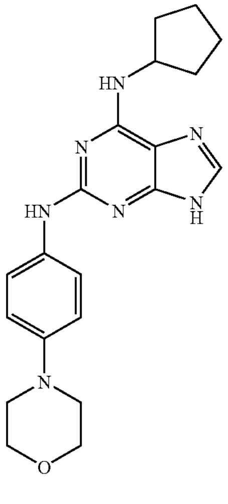
,
-continued
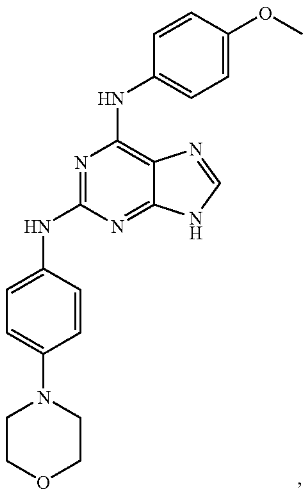
,
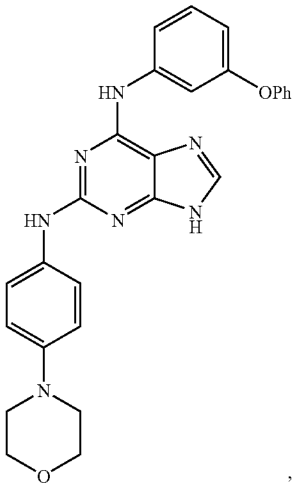
,
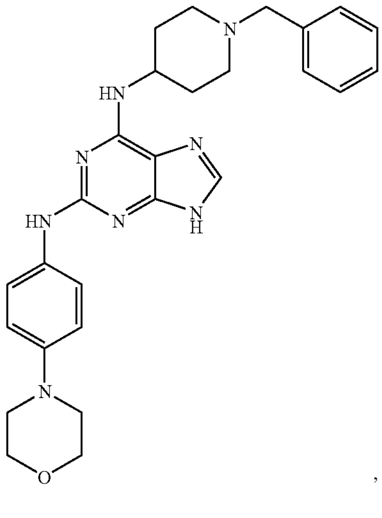
, -continued

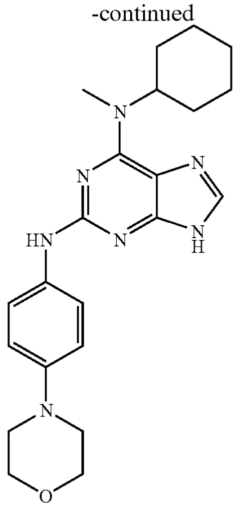

and

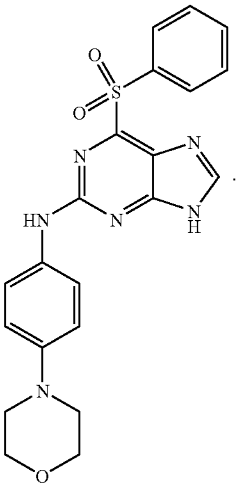

18. The method of claim 3, wherein said compound is

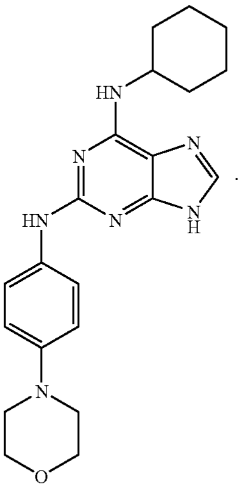

19. The method of claim 10, wherein said compound is

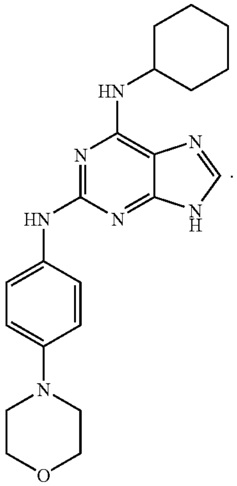

20. A method of inducing dedifferentiation of a lineage committed cell, the method comprising:

contacting a lineage committed mammalian myoblast cell, with a compound of Formula I having the following structure:

I

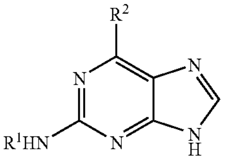

wherein:

$R^1$ is

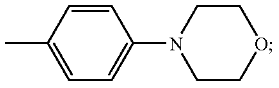

$R^2$ is a member selected from the group consisting of hydrogen, halogen and -L-$R^3$;

L is a member selected from the group consisting of —O—, —S— and —NH—;

$R^3$ is a member selected from the group consisting of $C_{1-4}$alkyl, $C_{3-8}$cycloalkyl, and aryl-$C_{1-2}$ alkyl substituted with 0-2 $R^{3a}$ groups that are independently selected from the group consisting of halogen, $C_{1-4}$alkyl, $C_{1-4}$alkoxy, —N($R^{3b}R^{3b}$), —$SO_2N(R^{3b}R^{3b})$, —C(O)N($R^{3b}R^{3b}$), and —O-aryl, or when said $R^{3a}$ groups are on adjacent ring atoms they are optionally taken together to form a member selected from the group consisting of —O—$(CH_2)_{1-2}$—O—, —O—$C(CH_3)_2$ $CH_2$— and —$(CH_2)_{3-4}$—; and each $R^{3b}$ group is a member that is independently selected from the group consisting of hydrogen and $C_{1-4}$ alkyl;

whereby the mammalian myoblast cell dedifferentiates into a multipotent stem cell.

* * * * *

UNITED STATES PATENT AND TRADEMARK OFFICE

CERTIFICATE OF CORRECTION

PATENT NO. : 7,592,177 B2
APPLICATION NO. : 10/985645
DATED : September 22, 2009
INVENTOR(S) : Shuibing Chen et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 280 days.

should read (*) Notice: Subject to any disclaimer, the term of this patent is extended or adjusted under 35 U.S.C. 154(b) by 442 days.

Signed and Sealed this

Fourth Day of May, 2010

David J. Kappos
*Director of the United States Patent and Trademark Office*